United States Patent
Chang et al.

(10) Patent No.: US 10,190,170 B2
(45) Date of Patent: Jan. 29, 2019

(54) MAKER FOR DIAGNOSING HER2 INHIBITOR RESISTANT CANCER, DIAGNOSTIC KIT COMPRISING SAME, AND METHOD FOR DIAGNOSING HER2 INHIBITOR RESISTANT CANCER

(71) Applicant: NATIONAL CANCER CENTER, Goyang-si, Gyeonggi-do (KR)

(72) Inventors: Hae Ryung Chang, Yeongdeungpo-gu (KR); Youme Gim, Gwanak-gu (KR); Hae Rim Jung, Goyang-si (KR); Seung Yoon Nam, Seongbuk-gu (KR); Jung sil Ro, Yongsan-gu (KR); Yon Hui Kim, Seocho-gu (KR)

(73) Assignee: NATIONAL CANCER CENTER, Goyang-si (KR)

( * ) Notice: Subject to any disclaimer, the term of this patent is extended or adjusted under 35 U.S.C. 154(b) by 0 days.

(21) Appl. No.: 14/726,390

(22) Filed: May 29, 2015

(65) Prior Publication Data
US 2015/0368722 A1  Dec. 24, 2015

(30) Foreign Application Priority Data
Jun. 20, 2014 (KR) .................. 10-2014-0075799

(51) Int. Cl.
C12Q 1/68 (2018.01)
G01N 33/574 (2006.01)
C12Q 1/6886 (2018.01)

(52) U.S. Cl.
CPC ..... *C12Q 1/6886* (2013.01); *G01N 33/57415* (2013.01); *C12Q 2600/106* (2013.01); *C12Q 2600/158* (2013.01); *G01N 2800/52* (2013.01)

(58) Field of Classification Search
None
See application file for complete search history.

(56) References Cited

FOREIGN PATENT DOCUMENTS

KR  1020100127780 A  12/2010
KR  1020120056939 A   6/2012

OTHER PUBLICATIONS

Budczies et al (Journal of Histochemistry & Cytochemistry, 59:146-157).*
GeneAnnot website, probesets for ENAH, Printed Sep. 1, 2016.*
Di Modugno et al 2006 (Clinical Cancer Research, 2006, 12:1470-1478).*
Di Modugno et al 2010 (PLoS ONE, 5:e15852, internet pp. 1-12).*
Di Modugno et al 2007 (Cancer Research, 2007, 67:2657-2665).*
Du et al (Eur J Gynaec, 2012, Oncology, 33: 455-458).*
Sharial et al (Annals of oncology, 2012, 23:3007-3016).*
Vaira et al (PNAS, 2010, 107:8352-8356).*
Giraud et al (Anticancer Research, 2012, 32:1323-1326).*
Barok et al (Molecular Cancer Ther. 2007, 6:2065-72).*
Milos Dokmanovic, Yi Shen, Tabetha M. Bonacci, et al., "Trastuzumab Regulates IGFBP-2 and IGFBP-3 to Mediate Growth Inhibition: Implications for the Development of Predictive Biomarkes for Trastuzumabab Resistance" Molecular Cancer Therapeutics 2011; vol. 10, No. 6, p. 917-928, published online www.aacrjournals.org.
Gelardi, T., et al., "Two novel human anti-ErbB2 immunoagents are active on trastuzumab-resistant tumours," *British Journal of Cancer*, vol. 102, Jun. 8, 2010, pp. 513-519, 7 pages.

* cited by examiner

*Primary Examiner* — Laura B Goddard
(74) *Attorney, Agent, or Firm* — Masuvalley & Partners

(57) ABSTRACT

The present invention relates to a composition for detecting a marker for diagnosing an HER2 inhibitor-resistant cancer, a diagnostic kit including same, and a method for detecting the marker. More particularly, the present invention relates to a composition for detecting a maker for diagnosing an HER2 inhibitor-resistant cancer, a diagnostic kit including same, and a method for detecting the marker, wherein the present invention allows presence and absence of resistance to an HER2 inhibitor, which is typically prescribed to an HER2-positive cancer patient, in an HER2-positive cancer patient to be determined in an easier manner with remarkably high reliability.

2 Claims, 13 Drawing Sheets

| | 19 KEGG pathways | |
|---|---|---|
| (1) | hsa05200 | pathways in cancer |
| (2) | hsa05211 | renal cell carcinoma |
| (3) | hsa04650 | natural killer cell mediated cytotoxicity |
| (4) | hsa04710 | circadian rhythm - mammal |
| (5) | hsa04115 | p53 signaling pathway |
| (6) | hsa04810 | regulation of actin cytoskeleton |
| (7) | hsa04210 | apoptosis |
| (8) | hsa04350 | TGF-beta signaling pathway |
| (9) | hsa03320 | PPAR signaling pathway |
| (10) | hsa04530 | tight junction |
| (11) | hsa04010 | MAPK signaling pathway |
| (12) | hsa04360 | axon guidance |
| (13) | hsa04310 | Wnt signaling pathway |
| (14) | hsa04060 | cytokine-cytokine receptor interaction |
| (15) | hsa04130 | SNARE interactions in vesicular transport |
| (16) | hsa04672 | intestinal immune network for IgA production |
| (17) | hsa05142 | Chagas disease |
| (18) | hsa05212 | pancreatic cancer |
| (19) | hsa04670 | leukocyte transendothelial migration |

FIG. 1

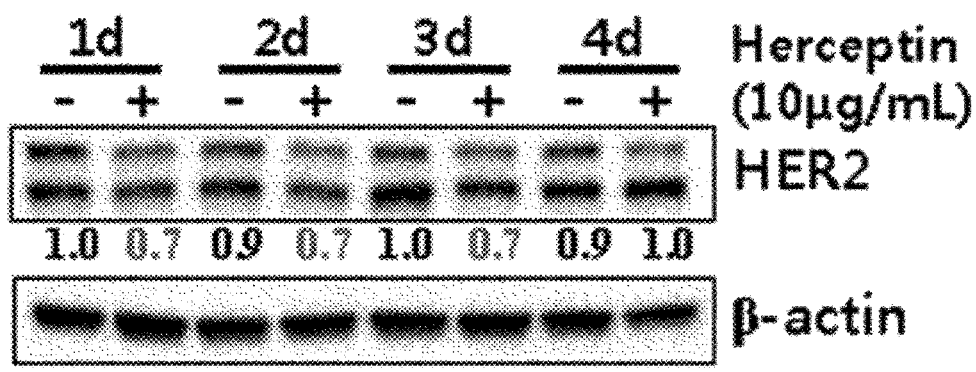
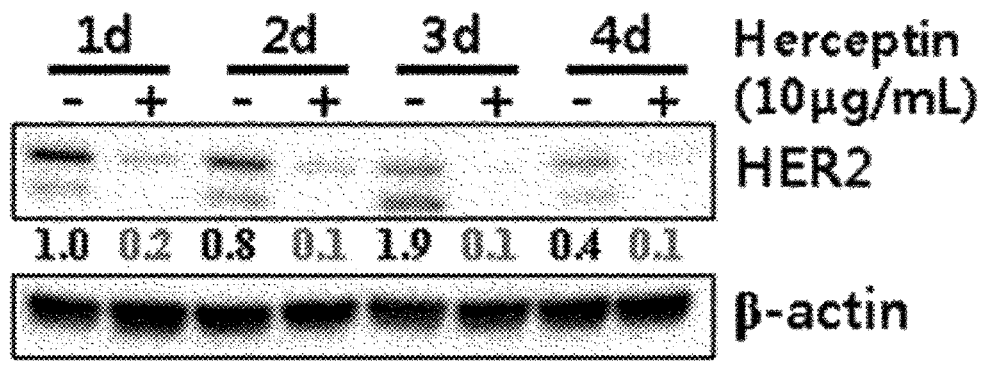
FIG. 13

MAKER FOR DIAGNOSING HER2 INHIBITOR RESISTANT CANCER, DIAGNOSTIC KIT COMPRISING SAME, AND METHOD FOR DIAGNOSING HER2 INHIBITOR RESISTANT CANCER

CROSS-REFERENCE TO RELATED APPLICATIONS

This U.S. non-provisional patent application claims priority under 35 U.S.C. § 119 of Korean Patent Application No. 10-2014-0075799, filed on Jun. 20, 2014, the entire contents of which are hereby incorporated by reference.

BACKGROUND OF THE INVENTION

The present invention relates to a marker for diagnosing an HER2 inhibitor-resistant cancer, a diagnostic kit including same, and a method for diagnosing an HER2 inhibitor-resistant cancer. More particularly, the present invention relates to a maker for diagnosing an HER2 inhibitor-resistant cancer, a diagnostic kit including same, and a method for diagnosing an HER2 inhibitor-resistant cancer, wherein the present invention allows presence and absence of resistance of an HER2-positive cancer patient against an HER2 inhibitor, which is typically prescribed to the HER2-positive cancer patient, to be determined in an easier way with remarkably high reliability.

Pharmaceutical industry continues to pursuit of therapeutic options for a novel drug which is more effective and more specific, or has little side effects than a drug administered nowadays. Due to genetic variance in the human population which causes a substantial difference in effects of many established drugs, an alternative of a drug therapy has been continuously developed. Therefore, although a wide range of drug therapy option is currently available, an additional therapy is required all times when a patient does not respond.

Typically, therapeutic paradigm used by a medical specialist is to prescribe a first-line drug resulted in the highest success rate as possible in disease treatment. When the first does not show an effect, an alternative drug therapy is successively prescribed. This paradigm is obviously not the best therapeutic method for certain diseases. For example, for a disease such as a cancer, commonly, a first treatment is the most important. Thus, there is an increased need to provide the best opportunity for successful treatment and to select a first drug which will be most effective for a disease of a particular patient. Cancer patients are no exception from the need. An approach through the most effective drug is required for cancer patients at the point of treatment.

HER family receptor tyrosine kinase is an important mediator of cell growth, differentiation, and survival. The receptor family includes four separate members including surface growth factor receptor (EGFR, ErbB1, or HER1), HER2 (ErbB2 or p185$^{neu}$), HER3 (ErbB3) and HER4 (ErbB4 or tyro2). Genes of the HER family have been reported to be involved in a malignant tumor of a human with a cause and effect relationship. Among them, P185$^{neu}$, which relates to HER2, is firstly isolated from neuroblastoma of a chemically treated rat as a product of a transformed gene. It has been found that an activated form of neu proto-oncogene is derived from a point mutation (mutation into glutamic acid from valine) in a transmembrane region of a protein coded therein. It has been already reported in documents such as [Slamon et al., Science, 235:177-182 (1987)], [Slamon et al., Science, 244:707-712 (1989)] that amplification of human homologue of the neu is observed in breast cancer and ovarian cancer, and relates to poor prognosis. Further, it has been persistently reported that overexpression of the HER2 is observed in other types of cancers including cancers in stomach, endometrium, salivary gland, lung, kidney, colon, thyroid, pancreas, and bladder, indicating that HER2 relates to the cancer above.

According to data reported so far, it has been known that about 15 to 20% of whole breast cancers have HER2 protein overexpression on cell surfaces thereof, and such tumors exhibit poorer prognosis than case where HER2 overexpression is not exhibited.

Thus, a number of drugs targeting to HER2 signaling typically have been developed as a tool of stopping growth of cancer cells showing HER2 protein overexpression. Herceptin (Trastuzumab), which is developed by Genentech, is one of these drugs. It has been demonstrated that herceptin is effective in prolong of survival of a patient who is diagnosed as advanced breast cancer showing HER2 overexpression. Also, it has been reported that herceptin reduces recurrence and death of a patient with early phase breast cancer having HER2 protein overexpression or HER2 gene amplification.

Consequently, when diagnosed as HER2-positive cancer, particularly, breast cancer, herceptin is typically prescribed. However, after prescription, a case appears in which cancer recurs or cancer metastasis occurs in a patient fully recovered from breast cancer after a certain period of time. It has been demonstrated that an occurrence of a mechanism of acquiring herceptin resistance is a cause of such case. As an example of the demonstration above, it has been found that, in transformed mice, new tumors are generated in most of mice within 1 to 9 months after HER2/neu transgene expression has been stopped; and the tumors are obviously variants of the tumors which are initially generated, and irrelevant to HER2/neu over expression, wherein the transformed mice are programmed such that mammary gland tumors are generated in a determined time by HER2/neu mutation, which is an oncogene, and then stopped.

Consequently, unstable genomes of cancer cells produce new alleles thereby having new properties which make proliferation ability to be enhanced. Then, the number of cells acquiring the genetic/epigenetic change is expanded to thereby induce cancer recurrence. Thus, after initially achieving success in reduction of tumor cell number, new types of cancer cells having resistance thereto are proliferated. Therefore, it is very important to determine presence and absence of resistance to the prescribed drug for cancer therapy.

However, a biomarker or diagnostic kit for determining whether a cancer patient has resistance to an HER2 inhibitor prescribed to an HER2-positive cancer patient (such as herceptin) are stilled during research and development so that there is no commercially available product. Also, a prototype product has a limitation in that high reliability is not achieved. Due to the current circumstance as above, in most cases, a costly drug such as lapatinib is inevitably prescribed to a HER2-positive cancer patient typically combined with herceptin. However, the combination therapy is not patient-customized therapy, but prescription including all number of cases which causes a problem of overtreatment. Further, the overtreatment has critical limitation, that is, incidence of side effects in a patient caused by prescription of an unnecessary drug and increased medical expenses.

Thus, it is urgently required to develop a biomarker, and diagnostic kit capable of easily determining whether a cancer patient has resistance to an HER2 inhibitor with high reliability.

SUMMARY OF THE INVENTION

The present invention is derived to overcome the limitation described above, and to provide a marker for diagnosing an HER2 inhibitor-resistant cancer, a diagnostic kit including same, and a method for diagnosing an HER2 inhibitor-resistant cancer, wherein the marker makes it possible, by determining presence and absence of resistance of an HER2-positive cancer patient to an HER2 inhibitor, which is typically prescribed to the HER2-positive cancer patient in a easier manner with high reliability, to provide an opportunity of full recovery through prescription of a second-line drug to the HER2-inhibitor-resistant cancer patient; to minimize a possibility of side effects incidence in the patient by preventing the HER2 inhibitor-resistant patient from being prescribed with the HER2 inhibitor; and to prevent increase in medical expense.

To overcome the limitation described above, the present invention provides a composition for detecting a marker for diagnosing an HER2 inhibitor-resistant cancer, the composition including: any one or more gene associated with HER2 inhibitor resistance among ATF4 (Entrez Gene ID 468), CHEK2 (Entrez Gene ID 11200), EGF (Entrez Gene ID 1950), EGLN2 (Entrez Gene ID 112398), ENAH (Entrez Gene ID 55740), FARP2 (Entrez Gene ID 9855) and RAD51 (Entrez Gene ID 5888); and an agent for measuring an expression level of mRNA or protein of the gene.

According to a preferred embodiment of the present invention, the agent for measuring an mRNA expression level includes any one or more among a primer pair and probe specifically binding to the gene, and the agent for measuring a protein expression level includes an antibody specific to the protein of the gene According to another preferred embodiment of the present invention, the HER2 inhibitor-resistant cancer includes any one or more selected from the group consisting of ovarian cancer, peritoneal cancer, fallopian tubal cancer, breast cancer, non-small cell lung cancer, squamous cell cancer, prostate cancer, stomach cancer and colorectal cancer According to another preferred embodiment of the present invention, the HER2 inhibitor may be Herceptin (trastuzumab), and the HER2 inhibitor-resistant cell line may be JIMT-1.

Further, to overcome the limitation described above, the present invention provides a kit for diagnosing an HER2 inhibitor-resistant cancer, the kit including the composition according to the present invention.

According to a preferred embodiment of the present invention, the kit may include any one or more among RT-PCR kit, DNA chip kit and protein chip kit.

Further, to overcome the limitation described above, the present invention provides a microarray for diagnosing an HER2 inhibitor-resistant cancer including any one or more gene associated with HER2 inhibitor resistance among ATF4 (Entrez Gene ID 468), CHEK2 (Entrez Gene ID 11200), EGF (Entrez Gene ID 1950), EGLN2 (Entrez Gene ID 112398), ENAH (Entrez Gene ID 55740), FARP2 (Entrez Gene ID 9855) and RAD51 (Entrez Gene ID 5888).

To overcome the limitation described above, the present invention provides a method for detecting a marker for diagnosing an HER2 inhibitor-resistant cancer, the method including: measuring an expression level of mRNA or protein of any one or more gene associated with HER2 inhibitor resistance among ATF4 (Entrez Gene ID 468), CHEK2 (Entrez Gene ID 11200), EGF (Entrez Gene ID 1950), EGLN2 (Entrez Gene ID 112398), ENAH (Entrez Gene ID 55740), FARP2 (Entrez Gene ID 9855) and RAD51 (Entrez Gene ID 5888) from a sample of a patient through the composition for detecting a marker according to the present invention; and comparing the measured expression level of mRNA or protein thereof with an expression level of mRNA or a protein of a corresponding gene in a control sample.

According to a preferred embodiment of the present invention, the measuring of an mRNA expression level is performed through at least any one method among reverse transcriptase polymerase reaction, competitive reverse transcriptase polymerase reaction, real time reverse transcriptase polymerase reaction, RNase protection analysis, Northern blotting, and DNA chip by including any one or more among primer pair and probe specifically binding to the gene, and the measuring of a protein expression level is performed through at least any one method among western blot, ELISA, radioimmunoassay, radial immunodiffusion, Ouchterlony immunodiffusion, rocket immunoelectrophoresis, immunohistochemical staining, immunoprecipitation assay, complement fixation assay, FACS and protein chip method by including an antibody specific to the corresponding protein.

Also, to overcome the limitation described above, the present invention provides a method for providing information about prognosis of an HER2-positive cancer patient about administration of an HER2 inhibitor, the method including determining whether resistance to the HER2 inhibitor arises or not by comparing an expression level of one or more of gene associated with HER2 inhibitor resistance among ATF4 (Entrez Gene ID 468), CHEK2 (Entrez Gene ID 11200), EGF (Entrez Gene ID 1950), EGLN2 (Entrez Gene ID 112398), ENAH (Entrez Gene ID 55740), FARP2 (Entrez Gene ID 9855) and RAD51 (Entrez Gene ID 5888) from a sample of the HER2-positive cancer patient who are taking the HER2 inhibitor with an expression level of mRNA or protein of the corresponding gene in the control sample.

Further, to overcome the limitation described above, the present invention provides a method for diagnosing presence and absence of HER2 inhibitor resistance, the method including determining presence and absence of HER2 inhibitor resistance by comparing an expression level of one or more gene associated with HER2 inhibitor resistance among ATF4 (Entrez Gene ID 468), CHEK2 (Entrez Gene ID 11200), EGF (Entrez Gene ID 1950), EGLN2 (Entrez Gene ID 112398), ENAH (Entrez Gene ID 55740), FARP2 (Entrez Gene ID 9855) and RAD51 (Entrez Gene ID 5888) from a sample of an HER2-positive cancer patient with an expression level of mRNA or protein of the corresponding gene in the control sample.

In addition, to overcome the limitation described above, the present invention provides a method for treating an HER2-positive tumor, the method including: determining whether resistance to an HER2 inhibitor is negative or not by comparing an expression level of one or more gene associated with HER2 inhibitor resistance among ATF4 (Entrez Gene ID 468), CHEK2 (Entrez Gene ID 11200), EGF (Entrez Gene ID 1950), EGLN2 (Entrez Gene ID 112398), ENAH (Entrez Gene ID 55740), FARP2 (Entrez Gene ID 9855) and RAD51 (Entrez Gene ID 5888) from a sample of an HER2-positive cancer patient with an expression level of mRNA or protein of the corresponding gene in the control sample; and administering the HER2 inhibitor to a patient diagnosed as negative to the HER2 inhibitor resistance in order to treat cancer cells.

Hereinafter, the terms used herein are defended as follows.

The term "subject" or "patient" used herein means any single organism requiring treatment, and includes human, cow, dog, guinea pig, rabbit, chicken, insect, and so forth. Also, the term includes any subject who does not have a clinical opinion of any disease and participates to clinical research test or epidemical research or is used as a control. In one embodiment of the present invention, the subject is a human.

Each of term "sample", "tissue sample", "patient sample", "patent cell or tissue sample" or "specimen" used herein means collection of similar cells obtained from tissue of the subject or patient. A source of tissue sample may be solid tissue, a tissue sample, biopsy, or aspiration from a fresh, frozen and/or preserved organ; blood or any blood component; body fluid such as cerebrospinal fluid, amniotic fluid, peritoneal effusion or interstitial fluid; or cells obtained after a period of time from pregnancy or development of a subject. The tissue sample may substantially contain a compound, which is not naturally mingled with tissue, such as a preservant, anticoagulation agent, buffer, fixer, nutrient, and antibiotic. Cells may be fixed in a typical manner, for example in a FFPE manner.

The term "marker" used herein refers to a nucleotide sequence or a coded product thereof (for example, protein) which is used as a standard point for identifying a locus or associated locus. The marker may be derived from a genome nucleotide sequence, expressed nucleotide sequence (for example, RNA, nRNA, mRNA, and cDNA, etc.), or a coded polypeptide. The term includes a nucleic acid sequence which is complementary to or flaked at the marker sequence, for example a nucleic acid which is used as a probe or primer pair capable of amplifying the marker sequence.

The term "nucleic acid" used herein means to include any DNA or RNA, for example a chromosome, mitochondria, virus and/or bacteria nucleic acid present in the tissue sample. The term includes one or both strand of a double strand nucleic acid molecule, and any fragment or part of an intact nucleic acid molecule.

The term "gene" used herein means any nucleic acid sequence or a part thereof having a functional role in protein coding, transcription or regulation of other gene expression. The gene may include all nucleic acids coding a functional protein, or a part of a nucleic acid coding or expressing protein. The nucleic acid sequence may include genomic abnormality in exon, intron, initiation or termination region, promoter sequence, other regulatory sequence, or a unique sequence adjacent to the gene.

The term "antibody" used herein is used with the broadest meaning, and specifically includes an intact monoclonal (monoclon) antibody, polyclonal antibody, multispecific antibody formed by at least two intact antibodies (for example, bispecific antibody), and antibody fragment exhibiting a desired biological activity.

The term "labeling agent" used herein means a compound or composition which is directly or indirectly conjugated or fused to a reagent, for example a nucleic acid probe or antibody to thereby facilitate detection of the conjugated or fused reagent. The labeling agent itself may be detected (for example, radioactive isotope labeling agent or fluorescent labeling agent) or may catalyze a chemical modification of detectable substrate compound or composition in the case of an enzyme labeling agent.

The term "cancer", and "tumor" used herein generally indicates or describes a physiological state of a mammal having characteristic of uncontrolled cell growth.

The term "inhibitor" used herein means a material which suppresses, blocks, or reduces expression or activity of a particular gene. An HER2 inhibitor used herein is a material which suppresses, blocks, or reduces expression or activity of HER2. An activation mechanism of the inhibitor is not specifically limited. Examples may include an organic or inorganic compound, polymer compound such as protein, carbohydrate, and lipid, and composite for various compounds.

According to the present invention, it is possible to more easily determine presence and absence of resistance of an HER2-positive cancer patient to an HER2 inhibitor (particularly, herceptin among HER2 inhibitors), which is typically prescribed to the HER2-positive cancer patient, with remarkably high reliability. In addition, since presence and absence of resistance to the HER2 inhibitor can be determined with high reliability, initially, the HER2 inhibitor is not prescribed to a patient determined to have resistance to the HER2 inhibitor, so that it is possible to reduce side effects of the HER2 inhibitor in a cancer patient due to unnecessary HER2 inhibitor prescription and increase in costs caused by overtreatment. Further, a cancer patient may be prevented from missing an appropriate treatment time by preventing inappropriate prescription for the cancer patient, and loss of an opportunity for treatment may be minimized through new prescription of a second-line drug. Still further, the present invention can be usefully applied to development of a novel anticancer drug which can overcome HER2 inhibitor resistance.

BRIEF DESCRIPTION OF THE DRAWINGS

FIG. 1 is a table showing various pathways involved in HER2 signaling including a gene associated with HER2 inhibitor resistance according to a preferred embodiment of the present invention.

FIG. 13 shows a result of evaluating expression levels of HER2 protein of the HER2 inhibitor-sensitive cell line and HER2 inhibitor resistant cell line depending on HER2 inhibitor treatment according to a preferred embodiment of the present invention.

DETAILED DESCRIPTION OF PREFERRED EMBODIMENTS

Figure 2:
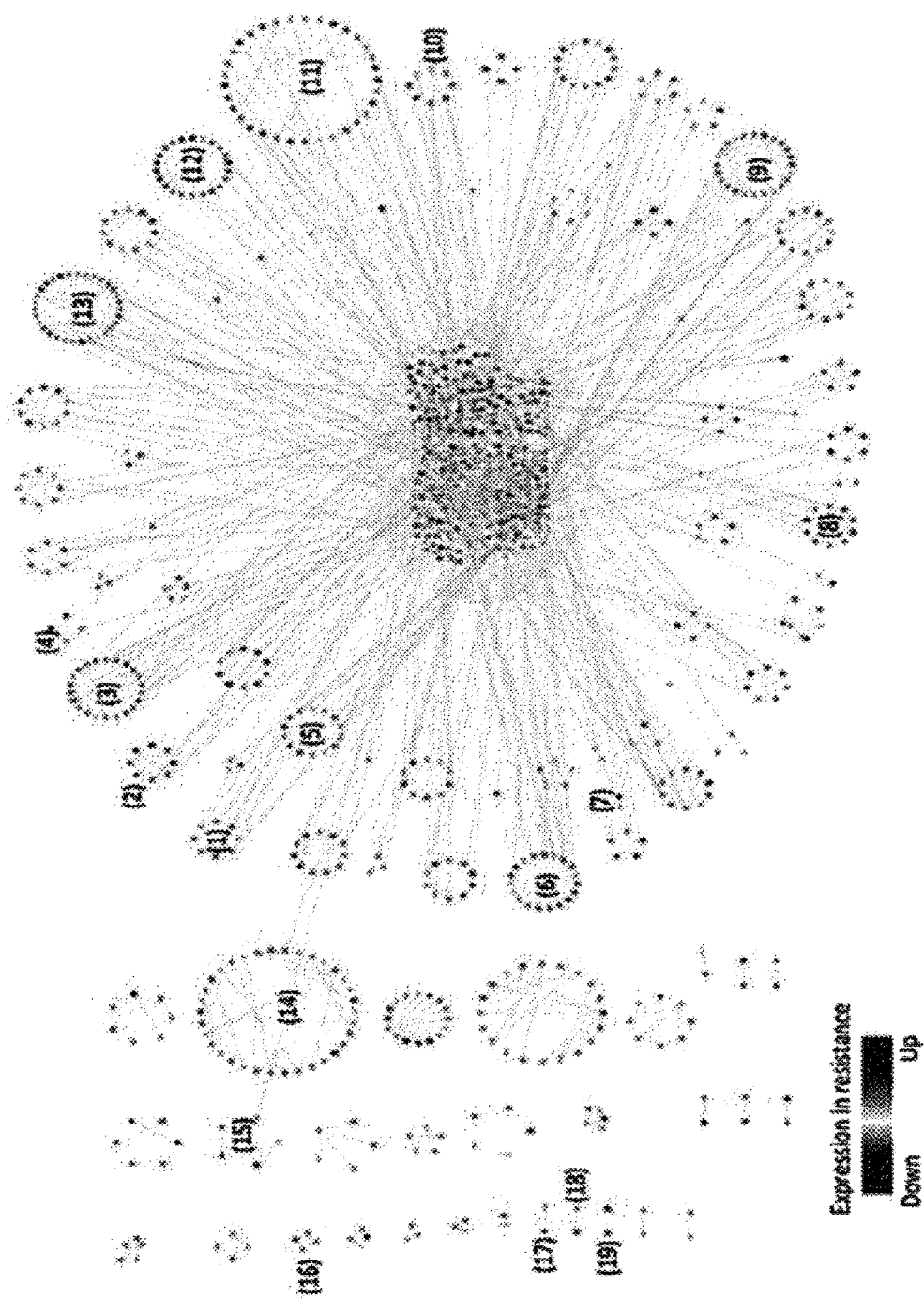
FIG. 2 is a schematic diagram showing signaling pathways involved in HER2 inhibitor resistance selected by the system biological approach according to a preferred embodiment of the present invention.

Hereinafter, the present invention will be described in more detail.

As described above, a biomarker or diagnostic kit capable of determining whether a cancer patient has resistance to an HER2 inhibitor prescribed to an HER2-positive cancer patient (such as herceptin) are stilled during research, so that there is no commercially available product. Also, a prototype product has a limitation in that high reliability is not achieved. Since it is difficult to diagnose presence and absence of resistance to an HER2 inhibitor through a maker which does not have high reliability, in most cases, a costly drug such as lapatinib is inevitably prescribed to the HER2-positive cancer patient typically combined with herceptin. However, the combination therapy is not patient-customized therapy, but prescription including all number of cases resulting in overtreatment, which leads critical limitations, that is, incidence of side effects in the patient caused by prescription of an unnecessary drug, and increase in medical expenses.

In the present invention, it has been tried to overcome limitations described above by providing a composition for detecting a marker for diagnosing an HER2 inhibitor-resistant cancer, the composition including an agent for measuring an expression level of mRNA or protein of a gene associated with HER2 inhibitor resistance which satisfies at least one conditions among (1) and (2) below. Through this, presence and absence of resistance to an HER2 inhibitor of an HER2-positive cancer patient is more easily determined with remarkably high reliability. From the determination, it is possible to provide an opportunity of full recovery to the patient having HER2 inhibitor resistance through prescription of a second-line drug; to minimize possibility of incidence of drug side effects in the patient by preventing the patient from being prescribed with the HER2 inhibitor; and to prevent increase in medical expense at the same time.

(1) when 10 μg/ml of an HER2 inhibitor is administered to an HER2 inhibitor-resistant cell line, after 24 hours, an expression amount of a gene associated with HER2 inhibitor resistance is increased by 9% or more with respect to an expression amount of the gene of the HER2 inhibitor-resistant cell line to which the HER2 inhibitor is not administered.

(2) when 10 μg/ml of an HER2 inhibitor is administered to an HER2 inhibitor-resistant cell line, after 48 hours, an expression amount of a gene associated with HER2 inhibitor resistance is increased by 5% or more with respect to an expression amount of the gene of the HER2 inhibitor-resistant cell line to which the HER2 inhibitor is not administered.

At first, it will be described about the HER2 inhibitor.

The HER2 inhibitor is a material which suppresses, blocks, or reduces expression or activity of HER2. An activation mechanism of the inhibitor is not specifically limited, and non-limiting examples of the inhibitor may include an organic or inorganic compound, polymer compound such as protein, carbohydrate, and lipid, and composite for various compounds. Preferably, the HER2 inhibitor may be herceptin (trastuzumab) which is typically and widely used. Consequently, the composition for detecting a marker according to the present invention may be remarkably useful to diagnose presence and absence of acquired resistance to herceptin.

In succession, a gene associated with HER2 inhibitor resistance will be described, wherein the gene relates to mRNA or protein thereof to be detected by the composition for detecting a marker according to the present invention.

At first, it will be described about a process of selecting a gene associated with HER2 inhibitor resistance.

Specifically, FIG. 1 is a table showing various pathways involved in HER2 signaling including a gene associated with HER2 inhibitor resistance according to a preferred embodiment of the present invention. The present inventors have selected an HER2 inhibitor resistant-network for selecting a gene associated with HER2 inhibitor resistance through system biological approach. To select the corresponding resistant network, [GSE15043] dataset stored in GEO of NCBI (USA) was used.

FIG. 2 is a schematic diagram showing signaling pathways involved in HER2 inhibitor resistance selected by the system biological approach according to a preferred embodiment of the present invention.

The pathway also includes PI3K/Akt and MAPK pathways which are known to be involved in resistance to an HER2 inhibitor such as herceptin. It can be found that pathways in the schematic diagram are closely connected each other via a cross-talk gene (specifically, which is a gene compartmentalized by yellow shadow in FIG. 2).

Figure 3:
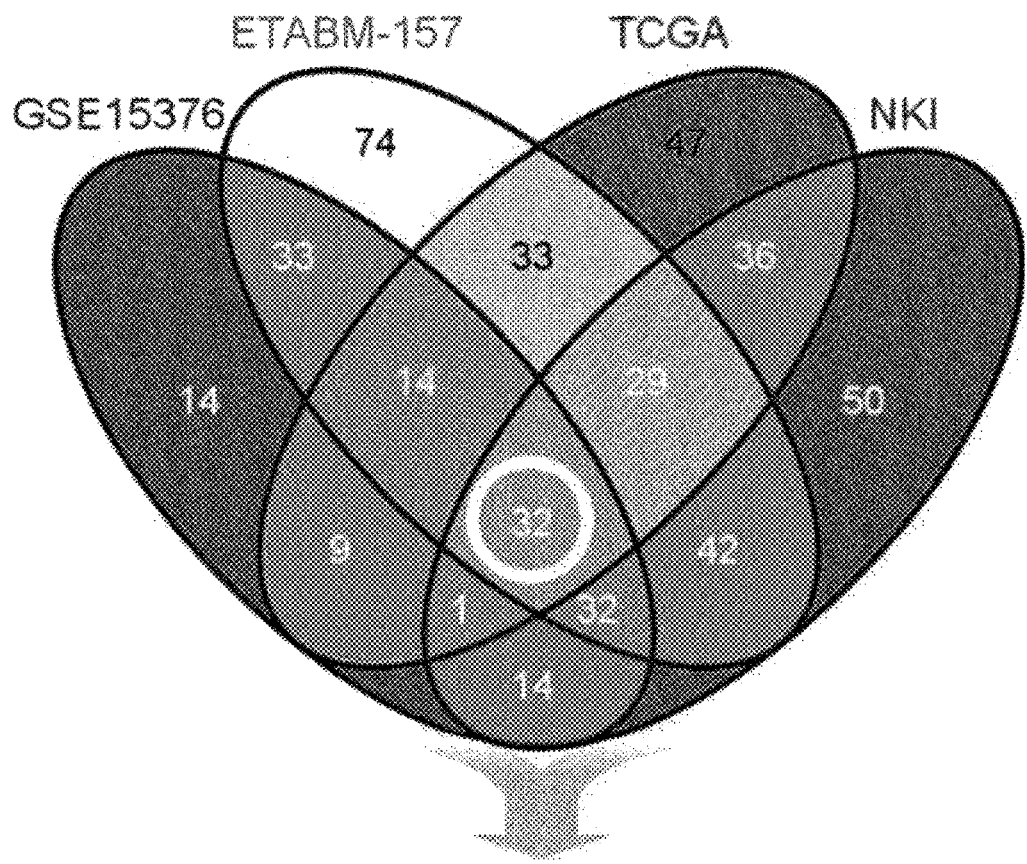
FIG. 3 is a schematic diagram showing a venn diagram which compares 4 datasets relating to HER2 inhibitor resistance with an HER2 inhibitor resistant-network derived from [GSE15043] dataset according to a preferred embodiment of the present invention.

FIG. 3 is a schematic diagram showing a venn diagram which compares 4 datasets associated with HER2 inhibitor resistance with the HER2 inhibitor-resistant network derived from [GSE15043] dataset according to a preferred embodiment of the present invention. Each set of the venn diagram means genes showing increased expression in both the network derived from [GSE15043] dataset and the dataset associated with the HER2 inhibitor resistance. By selecting the common gene in the HER2 inhibitor-resistant network in FIG. 2 and the datasets associated with HER2 inhibitor resistance of 4 authorities, 32 genes as shown in the table in FIG. 3 can be selected.

In succession, it will be described that the selected HER2 inhibitor resistance-associated gene can be a remarkably useful marker capable of diagnosing which cell has resistance to an HER2 inhibitor.

Specifically, it can be obviously demonstrated that the gene may be a useful marker for diagnosing presence and absence of HER2 inhibitor resistance by treating an HER2 inhibitor-resistant cell line and HER2 inhibitor-sensitive cell line with the HER2 inhibitor, and then measuring an expression amount of the gene associated with HER2 inhibitor resistance.

Prior to specifically describe, the HER2 inhibitor-resistant cell line and HER2 inhibitor-sensitive cell line will be described. The HER2 inhibitor-resistant cell line is an HER2-positive tumor cell acquiring resistance to an HER2 inhibitor, so that cell viability is not significantly reduced by HER2 inhibitor treatment, wherein the cell line may be an HER2 inhibitor-resistant cell line widely kwon in the art. Preferably, the cell line may be any one or more among JIMT-1, MCF7 and MDA-MB-231, and more preferably JIMT-1. It is obviously demonstrated that cell viability of the HER2 inhibitor-resistant cell line is not remarkably reduced by the HER2 inhibitor through the experiment in Example 4 described later. It has been found that, when JIMT-1 is treated with herceptin (which is an HER2 inhibitor), after 4 days, cell viability is reduced by only 15% or less with respect to the herceptin-untreated case (see FIG. 12).

The HER2 inhibitor-sensitive cell line an HER2-positive tumor cell having high drug response susceptibility to an HER2 inhibitor, so that cell viability is remarkably reduced by HER2 inhibitor treatment, wherein the cell line may be an HER2 inhibitor-sensitive cell line widely known in the art. Preferably, the HER2 inhibitor-sensitive cell line may be any one or more among SKBR3, BT474, and MDA-453, and more preferably SKBR3. It is obviously demonstrated that cell viability of the HER2 inhibitor-sensitive cell line is remarkably reduced by the HER2 inhibitor through the experiment in Example 4 described later, and it has been found that, when SKBR3 is treated with herceptin (which is an HER2 inhibitor), after 4 days, cell viability is reduced by more than 30% with respect to the herceptin-untreated case (see FIG. 12).

Figure 4:
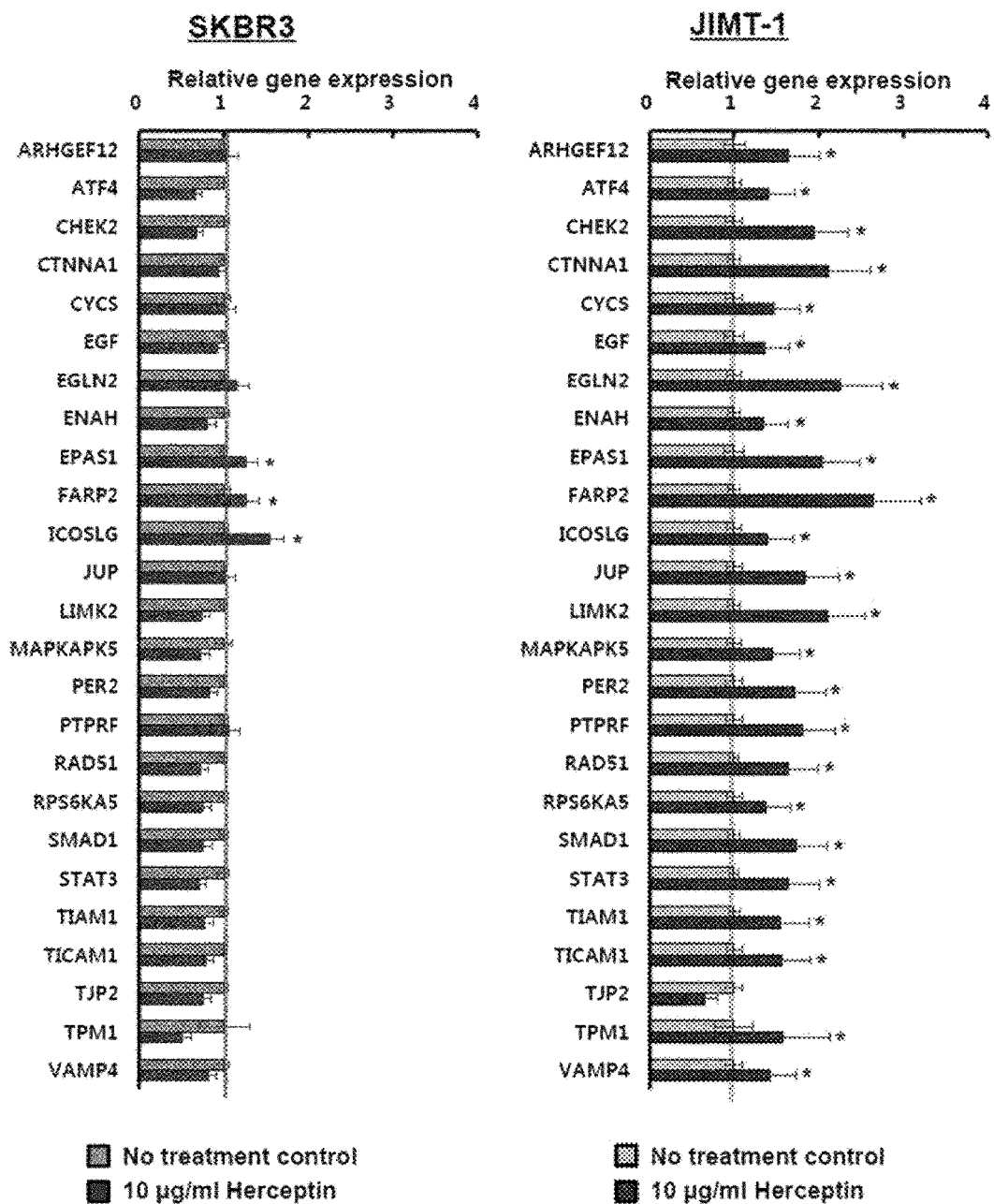
FIG. 4 is a graph showing amounts of expression of 25 genes associated with herceptin resistance after 24 hours of herceptin administration according to a preferred embodiment of the present invention.

FIG. 4 is a graph showing amounts of expression of 25 genes associated with herceptin resistance after 24 hours from 10 µg/ml herceptin administration into JIMT-1 (which is an HER2 inhibitor-resistant cell line) and SKBR3 (which is an HER2 inhibitor-sensitive cell line) according to a preferred embodiment of the present invention. It can be found that when JIMT-1 is treated with herceptin, expression amounts of most genes are increased in JIMT-1 which is an HER2 inhibitor-resistant cell line (e.g., an amount of expression of gene ARHGEF12 is increased by about 65%; an amount of expression of gene ATF4 is increased by about 40%; and an amount of expression of gene EGF is increased by about 37%), while, for SKBR3, which is an HER2 inhibitor-sensitive cell line, amounts of expression of most genes are reduced (e.g., an amount of expression of gene ATF4 is reduced by about 33%; and an amount of expression of gene CHEK2 is reduced by about 32%).

Figure 5:
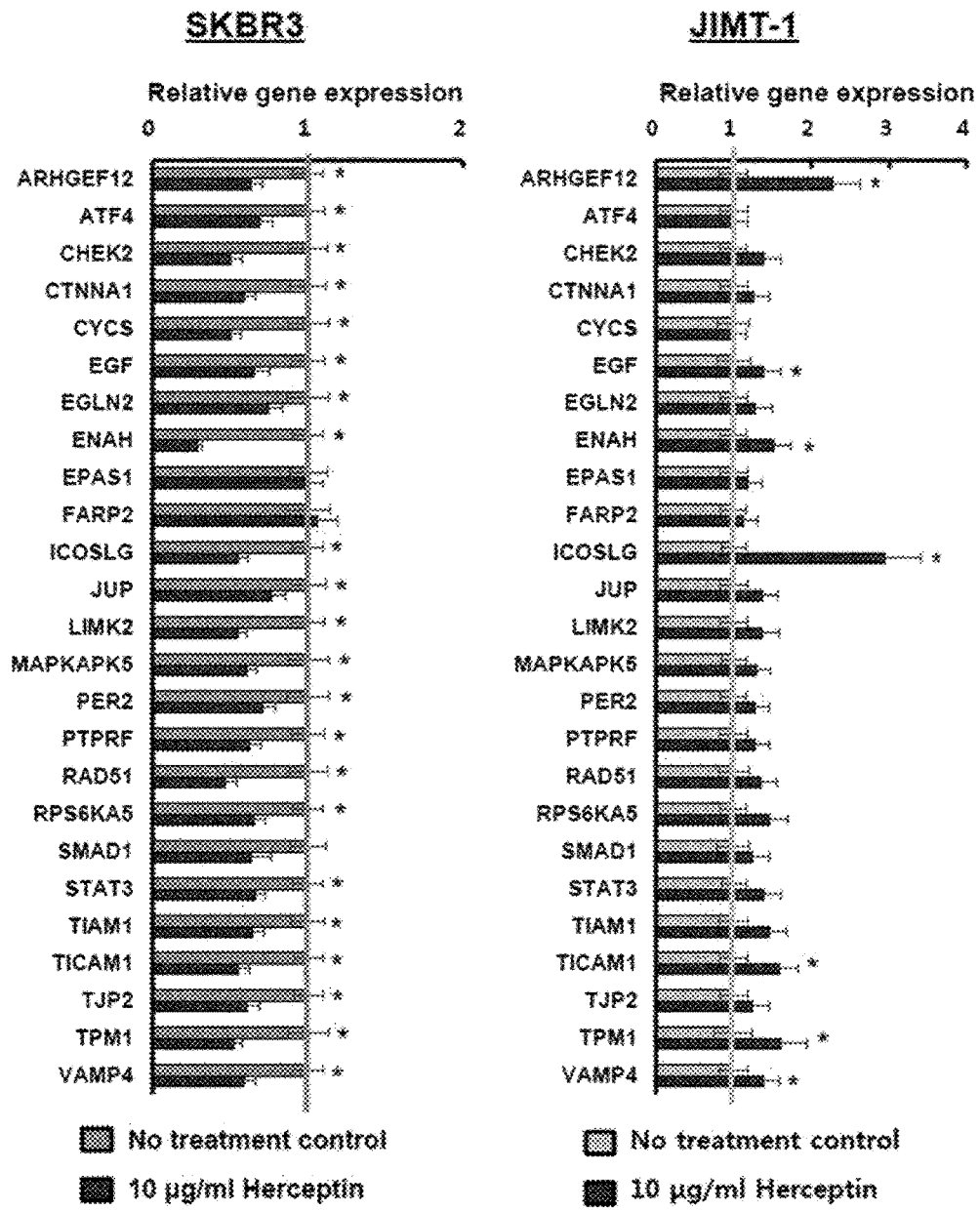
FIG. 5 is a graph showing amounts of expression of 25 genes associated with herceptin resistance after 48 hours of herceptin administration according to a preferred embodiment of the present invention.

FIG. 5 is a graph showing amounts of expression of 25 genes associated with herceptin resistance after 48 hours from 10 µg/ml herceptin administration into JIMT-1 (which is an herceptin-resistant cell line) and SKBR3 (which is an herceptin-sensitive cell line) according to a preferred embodiment of the present invention. It can be found that, for the herceptin-resistant cell line, i.e., JIMT-1, amounts of expression of almost genes are increased due to herceptin treatment (e.g., an amount of expression of gene ARHGEF12 is increased by about 128%; and an amount of expression of gene ENAH is increased by about 51%), while, for the herceptin-sensitive cell line, i.e., SKBR3, amounts of expression of almost genes are remarkably reduced (e.g., an amount of expression of gene ICOSLG is reduced by about 45%).

Through the experimental result as shown in FIGS. 4 and 5, it can be found that an appearance of expression of the gene associated with HER2 inhibitor resistance according to the present invention in the HER2 inhibitor resistant cell line differs from that in the HER2 inhibitor-sensitive cell line, and thus the gene may be useful as a marker to diagnose whether a certain cell is resistant or sensitive to the HER2 inhibitor.

The gene associated with HER2 inhibitor resistance may show time-dependent tendency. Specifically, the gene associated with HER2 inhibitor resistance may show tendency of up-regulation or down-regulation in a time-dependent manner in herceptin-resistant and herceptin-sensitive cell lines after herceptin administration.

More specifically, through the experimental results as shown in FIGS. 4 and 5, it can be found that, when 24 hours and 48 hours have been passed from herceptin administration, genes (such as gene ARHGER12 and ICOSLG) are remarkably upregulated in the herceptin-resistant cell line at 48 hours rather than 24 hours after herceptin administration, whereas most genes (such as gene ARHGER12, CHECK2, and CTNNA1) are remarkably down-regulated in the herceptin-sensitive cell line at 48 hours rather than 24 hours after herceptin administration. From the result, it can be found that some of genes associated with HER2 inhibitor resistance show time-dependent tendency which means upregulation and downregulation become stronger over time after HER2 inhibitor treatment.

Also, the time-dependent tendency of the gene associated with HER2 inhibitor resistance according to HER2 inhibitor treatment embraces other meaning. Specifically, it can be found that, TJP2 gene in the herceptin-resistant cell line of FIG. 4, i.e., JIMT-1, is downregulated at 24 hours after herceptin treatment unlike other genes; however the TJP2 gene in the same cell line is upregulated after 48 hours as well as other genes (see JIMT-1 in FIG. 5), and more specifically, an expression amount of TJP2 gene at 48 hours after herceptin treatment is increased by about 86% with respect to an expression amount of TJP2 gene after 24 hours. Also, it can be found that, ICOSLG gene in the herceptin-sensitive cell line of FIG. 4, i.e., SKBR3, is upregulated at 24 hours after herceptin treatment unlike other genes; however the ICOSLG gene in the same cell line is downregulated at 48 hours after herceptin treatment as well as other genes, and more specifically, an expression amount of ICOSLG gene at 48 hours after herceptin treatment is remarkably reduced by about 64% with respect to an expression amount of ICOSLG gene at 24 hours after.

The result as above may indicate that, although time required to upregulate or downregulate expression of the gene associated with HER2 inhibitor resistance after herceptin administration may differ depending on a degree of sensitivity of a cell line to herceptin, eventually, expression is downregulated in the herceptin-sensitive cell line and expression is upregulated in the herceptin-resistant cell line. It is considered that the gene associated with HER2 inhibitor resistance showing such tendency (for example, TJP2 and ICOSLG) is involved in downstream of HER2 signaling, and thus the time required to downregulate or upregulate expression of resistance by herceptin is getting longer than other genes associated with HER2 inhibitor resistance. Consequently, HER2 inhibitor (for example, herceptin) treatment may show time-dependent tendency which affects HER2 signaling not temporarily, but persistently to downstream of the HER2 signaling.

As described above, since the gene associated with HER2 inhibitor resistance, from which a maker to be detected by the composition for detecting a marker according to the present invention is derived, shows time-dependent tendency in an amount of expression of the gene due to the HER2 inhibitor treatment, the gene associated with HER2 inhibitor resistance is a gene which is included in various pathways involved in HER2 signaling, and upregulated by the HER2 inhibitor, wherein the gene satisfies at least one condition among (1) and (2) below.

(1) when 10 μg/ml of an HER2 inhibitor is administered to an HER2 inhibitor-resistant cell line, after 24 hours, an expression amount of a gene associated with HER2 inhibitor resistance is increased by 9% or more with respect to an expression amount of the gene of the HER2 inhibitor-resistant cell line to which the HER2 inhibitor is not administered.

(2) when 10 μg/ml of an HER2 inhibitor is administered to an HER2 inhibitor-resistant cell line, after 48 hours, an expression amount of a gene associated with HER2 inhibitor resistance is increased by 5% or more with respect to an expression amount of the gene of the HER2 inhibitor-resistant cell line to which the HER2 inhibitor is not administered.

Prior to describe each condition, it will be described why the marker satisfying any one condition among (1) and (2) above may be useful to determine presence and absence of HER2 inhibitor resistance. Gene associated with HER2 inhibitor resistance are respectively included in various pathways of HER2 signaling. In the pathways, a signal due to an HER2 inhibitor is directly/indirectly and simultaneously/sequentially transduced, and thus expression amounts of the genes inevitably show time-dependent tendency from treatment of the HER2 inhibitor. Moreover, even in the case where an expression amount of a certain gene is less than baseline at a certain time after HER2 treatment, for example, 24 hours after HER2 inhibitor treatment, the expression amount may be increased after 48 hours. Thus, in the case where condition (1) is not satisfied, it is not considered that the maker is inappropriate to determine presence and absence of HER2 inhibitor resistance. Consequently, in the case where any one of condition among (1) and (2) is satisfied, the maker may be useful to determine presence and absence of HER2 inhibitor resistance.

Therefore, for the gene associated with HER2 inhibitor resistance in condition (1) according to the present invention, when 10 μg/ml of an HER2 inhibitor is administered to an HER2 inhibitor-resistant cell line, after 24 hours, an expression amount of a gene associated with HER2 inhibitor resistance is increased by 9% or more with respect to an expression amount of the gene of the HER2 inhibitor-resistant cell line to which the HER2 inhibitor is not administered.

As shown in FIG. 4, it can be found that, for the herceptin-resistant cell line, i.e., JIMT-1 cells, expression amounts of most genes in the HER2 inhibitor-resistant cell line, i.e., JIMT-1, are increased at 24 hours after herceptin treatment, such that an expression amount of gene ARHGEF12 is increased by about 65%; an expression amount of gene ATF4 is increased by about 40%; and an expression amount of gene EGF is increased by about 37%. Through this, when 10 μg/ml of the HER2 inhibitor is administered to the HER2 inhibitor-resistant cell line, the expression amount of the gene associated with HER2 inhibitor resistance is increased by 9% or more after 24 hours with respect to the expression amount of the gene in the HER2 inhibitor-resistant cell line to which the HER2 inhibitor is not administered. Preferably, expression may be increased by 22% or more, and more preferably 35% or more. More enhanced reliability may be achieved through determination whether a cancer patient has resistance to an HER2 inhibitor or not by measuring an expression level of mRNA or protein thereof from the gene.

In succession, for the gene associated with HER2 inhibitor resistance in condition (2) according to the present invention, when 10 μg/ml of an HER2 inhibitor is administered to an HER2 inhibitor-resistant cell line, after 48 hours, an expression amount of a gene associated with HER2 inhibitor resistance is increased by 5% or more with respect to an expression amount of the gene of the HER2 inhibitor-resistant cell line to which the HER2 inhibitor is not administered.

As shown in FIG. 5, it can be found that, for the herceptin-resistant cell line, i.e., JIMT-1 cells, after 48 hours of herceptin treatment, an expression amount of gene ARHGEF12 is increased by about 128%; an expression amount of gene ENAH is increased by about 51%; and expression amount of gene TJP2, of which expression amount is reduced until 24 hours after herceptin treatment, is increased by about 35%. Through this, when 10 μg/ml of the HER2 inhibitor is administered to the HER2 inhibitor-resistant cell line, after 48 hours, the expression amount of the gene associated with HER2 inhibitor resistance is increased by 5% or more with respect to the expression amount of the gene in the HER2 inhibitor-resistant cell line to which the HER2 inhibitor is not administered. The expression may preferably be increased by 9% or more, and more preferably 13% or more. More enhanced reliability may be achieved by determining whether a cancer patient has resistance to an HER2 inhibitor or not by measuring an expression level of mRNA or protein thereof from the gene.

According to a preferred embodiment of the present invention, the gene associated with HER2 inhibitor resistance, which satisfies at least one condition among (1) and (2) above, may include any one or more gene selected from the group consisting of ARHGEF12 (Entrez Gene ID 23365), ATF4 (Entrez Gene ID 468), CCL22 (Entrez Gene ID 6367), CHEK2 (Entrez Gene ID 11200), CTNNA1 (Entrez Gene ID 1495), CYCS (Entrez Gene ID 54205), EGF (Entrez Gene ID 1950), EGLN2 (Entrez Gene ID 112398), ENAH (Entrez Gene ID 55740), EPAS1 (Entrez Gene ID 2034), FARP2 (Entrez Gene ID 9855), FES (Entrez Gene ID 2242), FRAT1 (Entrez Gene ID 10023), ICOSLG (Entrez Gene ID 23308), JAM3 (Entrez Gene ID 83700), JUP (Entrez Gene ID 3728), LIMK2 (Entrez Gene ID 3985), MAPK10 (Entrez Gene ID 5602), MAPKAPK5 (Entrez Gene ID 8550), MMP9 (Entrez Gene ID 4318), NFATC4 (Entrez Gene ID 4776), PER2 (Entrez Gene ID 8864), PTPRF (Entrez Gene ID 5792), RAD51 (Entrez Gene ID 5888), RPS6KA5 (Entrez Gene ID 9252), SMAD1 (Entrez Gene ID 4086), STAT3 (Entrez Gene ID 6774), TIAM1 (Entrez Gene ID 7074), TICAM1 (Entrez Gene ID 148022), TJP2 (Entrez Gene ID 9414), TPM1 (Entrez Gene ID 7168) and VAMP4 (Entrez Gene ID 8674). For the gene, it can be found that the expression amount of the gene shows time-dependent tendency according to HER2 inhibitor treatment as described above through FIGS. 4 and 5.

Figure 6:
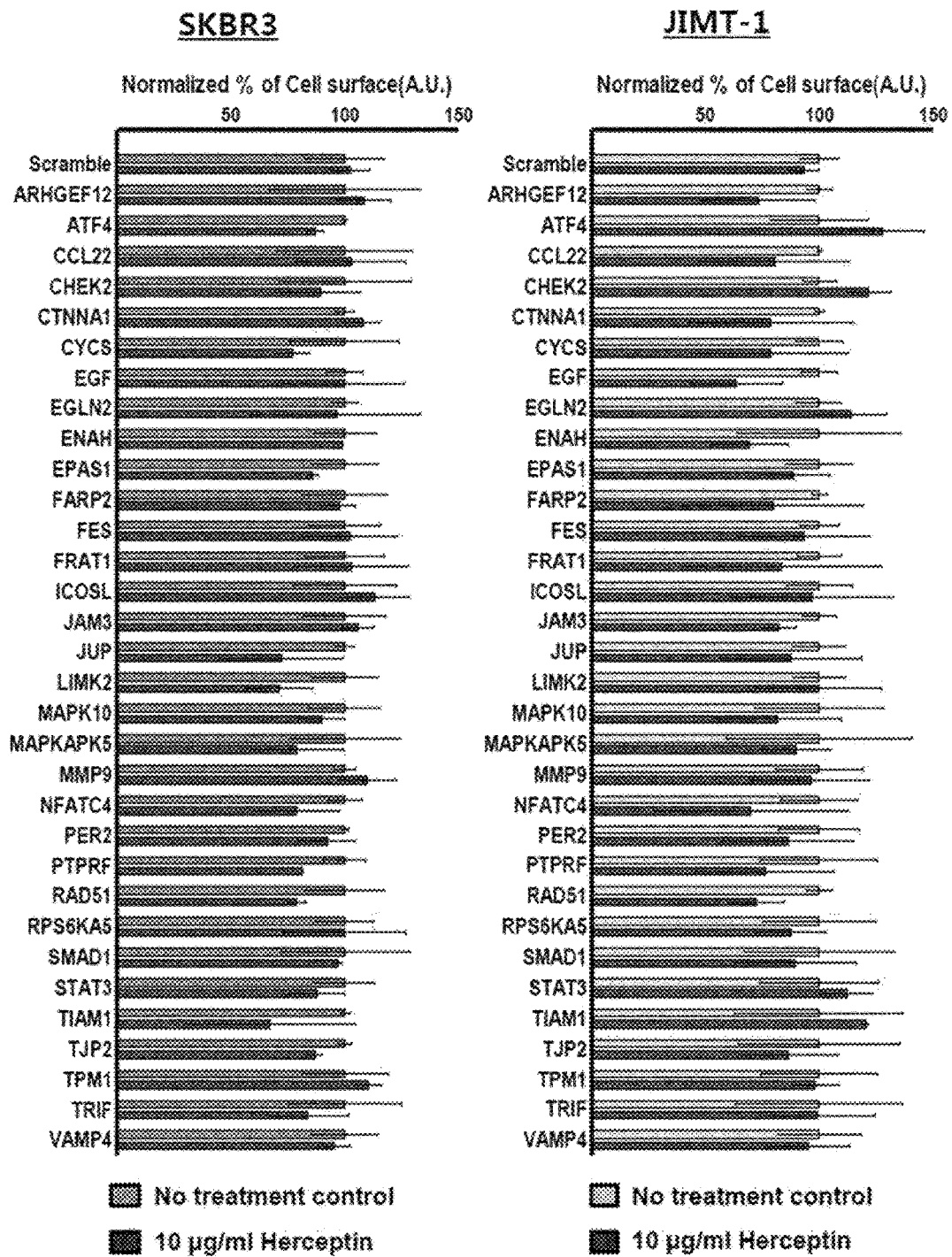
FIG. 6 is a graph showing a cell viability test of an HER2 inhibitor-resistant cell line and HER2 inhibitor-sensitive cell line, in which a gene associated with HER2 inhibitor resistance is knocked-down, according to a preferred embodiment of the present invention.

Further, to evaluate whether the 32 genes associated with HER2 inhibitor resistance substantially affect HER2 inhibitor resistance, the present inventors have evaluated cell viability after knocking down any one of genes among the 32 genes associated with HER2 inhibitor resistance, and then treating an HER2 inhibitor. Specifically, FIG. 6 is a graph showing a cell viability test of an HER2 inhibitor-resistance cell line and HER2 inhibitor-sensitive cell line, in which a gene associated with HER2 inhibitor resistance is knocked-down. It can be found that for a cell in which any one of gene among 32 genes is knocked-down, although the cell has resistance to an HER2 inhibitor, cell viability is reduced by the HER2 inhibitor. From the result, it can be found that: the cell, in which any one of 32 genes associated with HER2 inhibitor resistance is knocked-down, recovers sensitivity to the HER2 inhibitor, even the cell is resistant cell to the HER2 inhibitor; the 32 genes are obviously associated with HER2 inhibitor resistance; and the 32 genes are more useful maker to determine presence and absence of HER2 inhibitor resistance.

In addition, presence and absence of HER2 inhibitor resistance can be more reliably determined by a gene associated with HER2 inhibitor resistance which further satisfies condition (3) below in addition to conditions (1) and (2) described above.

(3) when 10 μg/ml of an HER2 inhibitor is administered to an HER2 inhibitor-sensitive cell line, after 48 hours, an expression amount of a gene associated with HER2 inhibitor resistance is reduced by 17% or more with respect to an expression amount of the gene of the HER2 inhibitor-sensitive cell line to which the HER2 inhibitor is not administered.

In the condition (3), the HER2 inhibitor-sensitive cell line may preferably be SKBR3, and the HER2 inhibitor may be herceptin. Specifically, in FIG. 5, it can be found that, after 48 hours from 10 μg/ml of herceptin treatment, expression amounts of almost genes in the herceptin-sensitive cell line, i.e., SKBR3 are remarkably reduced, such that an expression amount of gene ICOSLG is reduced by about 45%. In contrary, it can be found that, after 48 hours from herceptin treatment, an expression amount of the corresponding gene, e.g., ICOSLG in the HER2 inhibitor-resistant cell line, i.e., JIMT-1 is increased by about 194%. Therefore, the gene further satisfying the condition (3) above may be advantageous in more clear determination of presence and absence of HER2 inhibitor resistance, since expression degrees are clearly distinguished when the HER2 inhibitor is treated depending whether a cell has resistance to the HER2 inhibitor or not.

Figure 7:
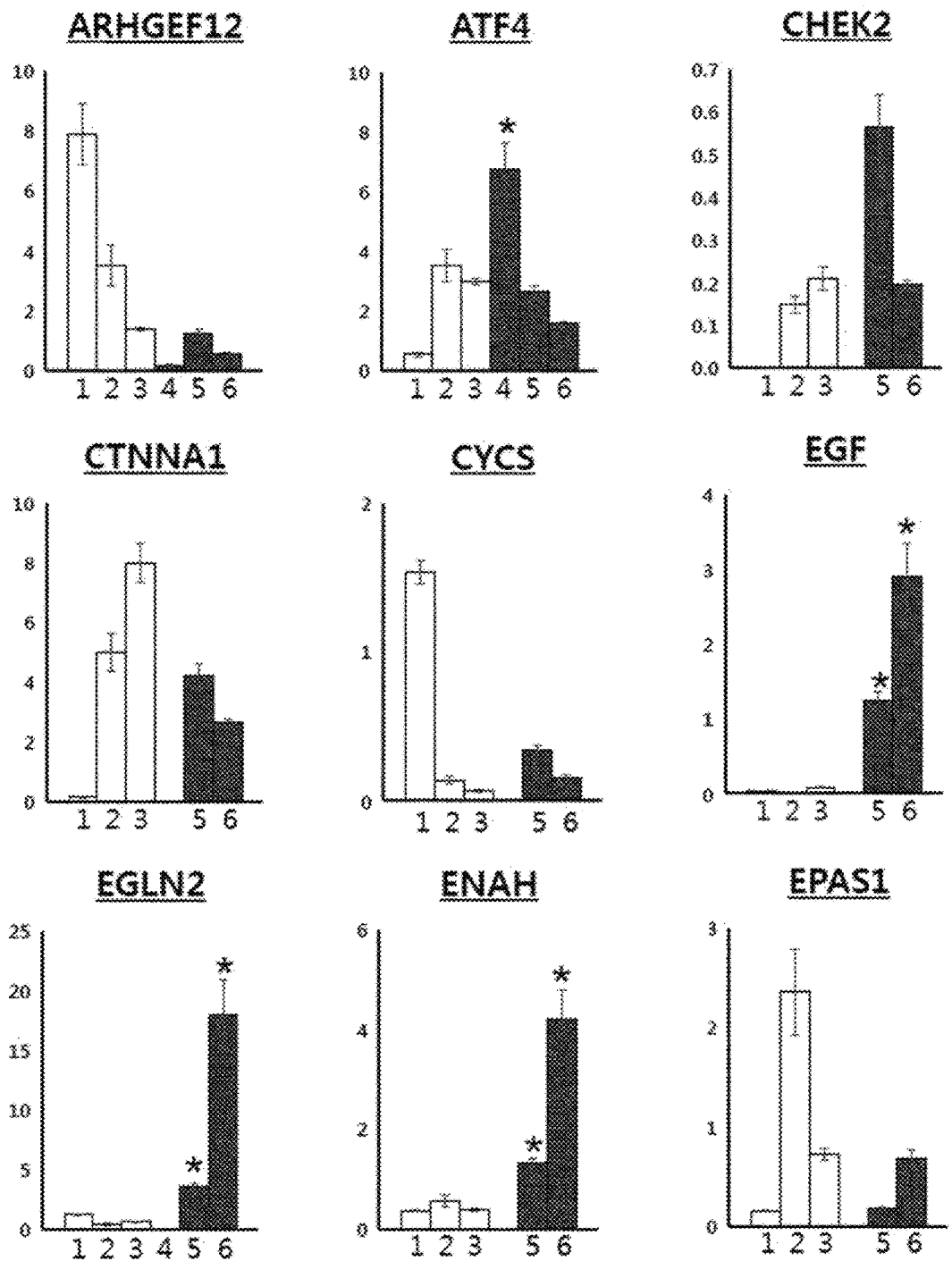
FIG. 7 is a graph showing a clinical test result on a gene associated with HER2 inhibitor resistance according to a preferred embodiment of the present invention.
Figure 8:
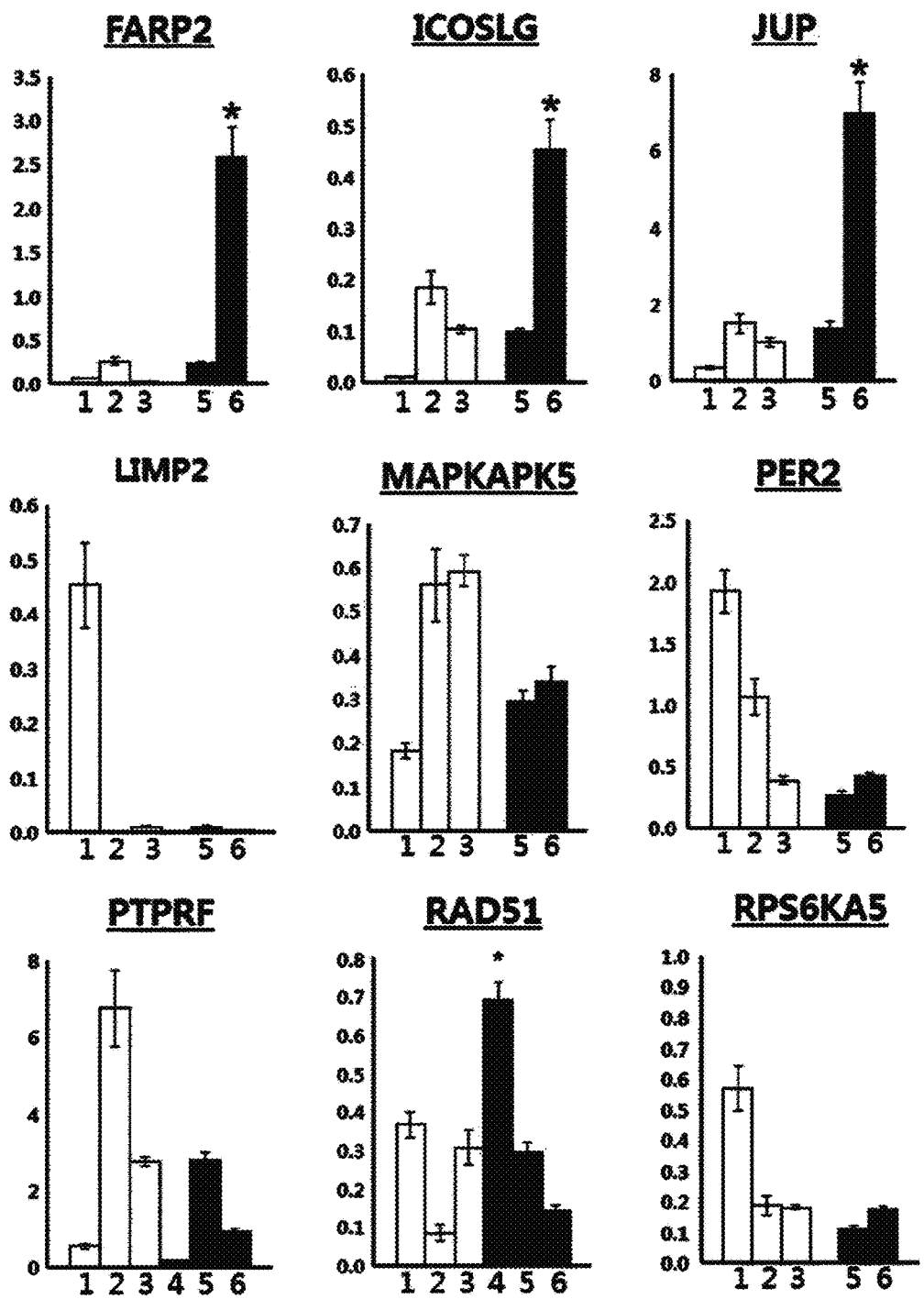
FIG. 8 is a graph showing a clinical test result on a gene associated with HER2 inhibitor resistance according to a preferred embodiment of the present invention.
Figure 9:
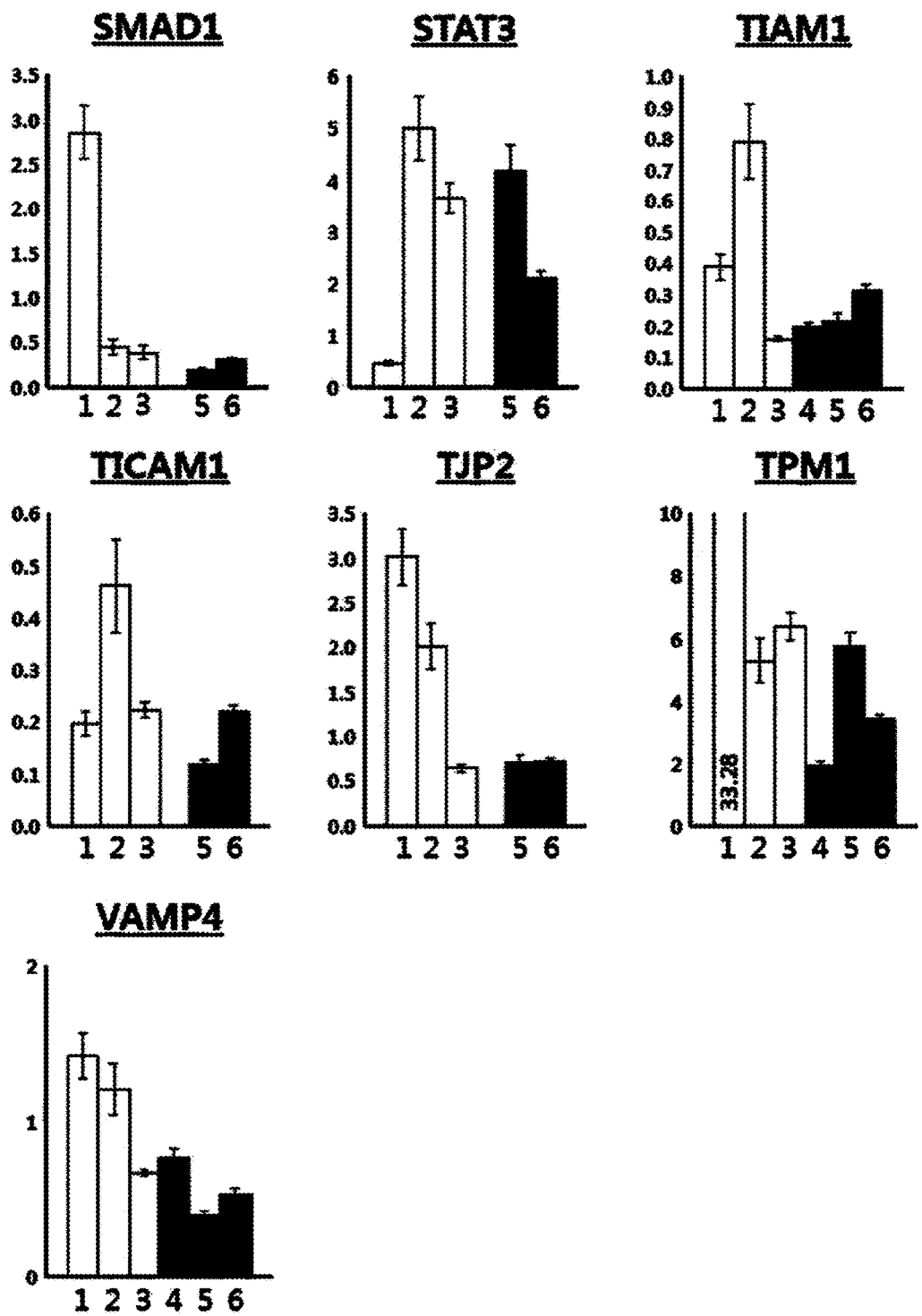
FIG. 9 is a graph showing a clinical test result on a gene associated with HER2 inhibitor resistance according to a preferred embodiment of the present invention.

Some of the 32 genes associated with HER2 inhibitor resistance may be a remarkably useful marker to actually diagnose presence and absence of HER2 inhibitor resistance in clinically. Specifically, FIGS. 7 to 9 are graphs showing clinical test results on genes associated with HER2 inhibitor resistance, wherein expression degrees for each of 32 genes of cancer cells, which are taken from 3 patients sensitive to an HER2 inhibitor and 3 patients resistant to the HER2 inhibitor, are evaluated. As a result, can be found that any one or more gene selected from the group consisting of ATF4 (Entrez Gene ID 468), CHEK2 (Entrez Gene ID 11200), EGF (Entrez Gene ID 1950), EGLN2 (Entrez Gene ID 112398), ENAH (Entrez Gene ID 55740), FARP2 (Entrez Gene ID 9855) and RAD51 (Entrez Gene ID 5888) is expressed in a remarkably low level in cancer cells taken from 3 patient group sensitive to the HER2 inhibitor, while the gene is remarkably overexpressed in cancer cells taken from 3 patient group resistant to the HER2 inhibitor. Therefore, for the 7 genes among 32 genes associated with HER2 inhibitor resistance, since expression amounts of the corresponding genes may be significantly upregulated or downregulated depending whether the cells have resistance to the HER2 inhibitor or not, the 7 genes are remarkably efficient to diagnose whether a cancer patient has resistance to the HER2 inhibitor, and also reliability of diagnosis may be high.

In sequence, it will be described about an agent for measuring an expression level of mRNA or protein of the gene associated with HER2 inhibitor resistance described above.

The wording "an agent for measuring an expression level of a gene associated with HER2 inhibitor resistance" used herein means a molecule, which can be used to detect a maker by evaluating an expression level of the gene associated with HER2 inhibitor resistance, preferably an antibody, primer or probe specific to the marker, wherein the gene associated with HER2 inhibitor resistance is a maker of which expression is upregulated by an HER2 inhibitor.

It is possible to know an expression level of the gene associated with HER2 inhibitor resistance by evaluating an expression level of mRNA of the gene associated with HER2 inhibitor resistance or evaluating an expression level of a protein coded by the gene. The wording "measurement of an mRNA expression level" herein is a process of evaluating presence and absence and an expression degree of mRNA of the gene associated with HER2 inhibitor resistance, which is a maker, in a biological sample in order to determine presence and absence of HER2 inhibitor resistance, wherein the expression degree can be evaluated by measuring an amount of mRNA. Analysis methods for measurement includes, RT-PCR, competitive RT-PCR, real-time RT-PCR, RNase protection assay (RPA), Northern blotting, and DNA chip, etc., but not limited thereto.

The wording "measurement of a protein expression level" herein is a process of evaluating presence and absence and an expression degree of a protein expressed from the gene associated with HER2 inhibitor resistance, which is a maker, in a biological sample in order to determine presence and absence of HER2 inhibitor resistance, wherein an amount of the protein is evaluated by using an antibody specifically binding to the protein of the gene. Analysis methods for measurement includes Western-blot, enzyme linked immunosorbent assay (ELISA), radioimmunoassay (RIA), radioimmunodiffusion, Ouchterlony immunodiffusion, rocket immunoelectrophoresis, immunohistochemical staining, immunoprecipitation assay, complement fixation assay, FACS, protein chip, etc., but not limited thereto.

At first, an agent of measuring an mRNA level of the gene may preferably be a primer pair or probe, and a person skilled in the art may design the primer or probe which specifically amplifies a particular region of these gene based on a gene sequence according to information about the gene associated with HER2 inhibitor resistance, preferably 32 genes associated with HER2 inhibitor resistance.

The term "primer" herein means a short nucleic acid sequence having a short free 3 terminal hydroxyl group; capable of forming a base pair with a complementary template; and playing a role as an initiation point for replication of the template strand. The primer initiates DNA synthesis in an appropriate buffer and under appropriate temperature in the presence of 4 different types of nucleoside triphosphate and a regent for polymerization (i.e., DNA polymerase or reverse transcriptase). In the present invention, presence and absence of HER2 inhibitor resistance may be determined by: performing PCR amplification by using sense and antisense primers of polynucleotides of the gene associated with HER2 inhibitor resistance; and measuring presence and absence of production of the desired product, and a level of production. The PCR condition, length of sense and antisense primers may be modified based on those known in the art, and not specifically limited in the present invention.

The term "probe" herein means a nucleic acid fragment such as RNA or DNA, which corresponds to several bases (if, short) to several hundred bases (if, long), capable of specifically binding to mRNA, wherein the probe is labeled such that presence and absence of particular mRNA can be evaluated. The probe may be constructed in a form of oligonucleotide probe, single stranded DNA probe, double stranded DNA probe, and RNA probe, etc. In the present invention, hybridization is performed by using a probe complementary to the gene associated with HER2 inhibitor resistance, and thus presence and absence of HER2 inhibitor resistance is diagnosed depending whether hybridization occurs or not. Selection of an appropriate probe and hybridization condition may be modified from those of known in the art, and not specifically limited in the present invention.

The primer or probe of the present invention may be chemically synthesized by using phosphoramidite solid support method or other widely known methods. The nucleic acid sequence may be modified by using various tools known in the art. Non-limiting examples of such modifications include methylation, capping, substitution with one or more cognate of natural nucleotide and modification between nucleotides such as modification with an uncharged linker (e.g., methyl phosphonate, phosphotriester, phosphoramidite, and carbamate, etc.) or a charged linker (e.g., phosphorothioate, and phosphorodithioate, etc.).

An agent of measuring a protein level may preferably be an antibody.

The term "antibody" herein is a known term in the art, and means a specific protein molecule indicated by an antigenicity region. For the purpose of the present invention, the antibody means an antibody specifically binding to a protein expressed by the gene associated with HER2 inhibitor resistance, which is a marker of the present invention, and the antibody may be prepared by using the preparation method widely known in the art. The antibody includes a part of peptide which may be made from the protein. The part of peptide of the present invention includes at least 7 amino acids, preferably 9 amino acids, and more preferably 12 or more amino acids. A form of the antibody of the present invention is not specifically limited but includes polyclonal antibody, monoclonal antibody or a part thereof as long as having an antigen binding property, and all immunoglobulin antibodies. Further, the antibody of the present invention includes a specific antibody such as a humanized antibody.

In addition, for the composition for detecting a marker for diagnosing an HER2 inhibitor-resistant cancer according to the present invention, the cancer in which resistance arises against an HER2 inhibitor may preferably be a cancer including any one or more selected from the group consisting of ovarian cancer, peritoneal cancer, fallopian tubal cancer, breast cancer, non-small cell lung cancer, squamous cell cancer, prostate cancer, stomach cancer, breast cancer and colorectal cancer. However, regardless of a subjective organ or specific form of the cancer, an HER2-positive cancer may be included, and not limited to the type described above.

The present invention includes a kit for diagnosing an HER2 inhibitor resistant cancer, the kit including the composition for detecting a marker for diagnosing an HER2 inhibitor-resistant cancer according to the present invention as described above.

The kit can detect a marker by evaluating an expression level of mRNA or protein of the gene associated with HER2 inhibitor resistance which is a marker to diagnose an HER2 inhibitor-resistant cancer. The kit includes composition liquid of one or more types of other components or a device appropriate for the analysis method as well as a primer, probe, or an antibody selectively recognizing a maker in order to measure an expression level of the marker which makes it possible to diagnose the HER2 inhibitor-resistant cancer.

Specifically, at first, the kit for measuring an expression level of mRNA of the gene associated with HER2 inhibitor resistance may include an essential element required to perform RT-PCR. The RT-PCR kit may include a test tube or other appropriate container, reaction buffer (which has various pH and magnesium concentrations), deoxynucleotides (dNTPs), enzyme such as Taq-polymerase and reverse transcriptase, DNase and RNase inhibitor, DEPC-water, and sterilized water in addition to each primer pair designed by a person skill in the art to become specific to the marker gene. Also a primer pair specific to 18s rRNA, which is used as a quantification control, may be included. Further, the kit of the present invention may be a kit for detecting a diagnostic marker, the kit including an essential element required to perform DAN chip. The DNA chip kit may include a base to which cDNA corresponding to a gene or a fragment thereof is bound as a probe, and the base may include cDNA which corresponds to a quantification control gene or a fragment thereof.

The kit for measuring a protein expression level of the gene associated with HER2 inhibitor resistance may include a substrate, appropriate buffer, secondary antibody labeled with a luminescent enzyme or fluorescent material, and luminescent substrate to immunologically detect an antibody. As the substrate, a nitrocellulose membrane, 96-well plate synthesized by polyvinyl resin, 96-well plate synthesized by polystyrene resin, and slide glass made by glass, etc., may be used. As the luminescent enzyme, peroxidase, and alkaline phosphatase, etc., may be used. As the fluorescent material, FITC and RITC, etc. may be used. As the luminescent substrate liquid, 2,2'-azino-bis-(3-ethylbenzthiazoline-6-sulfonic acid) (ABTS), 0-phenylenediamine (OPD), or tetramethylbenzidine (TMB), etc., may be used.

Further, the present invention includes a microarray for diagnosing an HER2 inhibitor-resistant cancer, the microarray including a gene associated with HER2 inhibitor resistance which satisfies at least one of conditions (1) and (2) below. Through the microarray, presence and absence of HER2 inhibitor resistance can be determined with high reliability.

(1) when 10 µg/ml of an HER2 inhibitor is administered to an HER2 inhibitor-resistant cell line, after 24 hours, an expression amount of a gene associated with HER2 inhibitor resistance is increased by 9% or more with respect to an expression level of the gene of the HER2 inhibitor-resistant cell line to which the HER2 inhibitor is not administered.

(2) when 10 µg/ml of an HER2 inhibitor is administered to an HER2 inhibitor-resistant cell line, after 48 hours, an expression amount of a gene associated with HER2 inhibitor resistance is increased by 5% or more with respect to an expression level of the gene of the HER2 inhibitor-resistant cell line to which the HER2 inhibitor is not administered.

The specific description about conditions (1) and (2) are same as described above so that the descriptions are omitted. Hereinafter, the microarray will be described in more detail.

The microarray may include DNA or RNA polynucleotide. The microarray includes a typical microarray-forming composition or device except that the microarray includes a polynucleotide of the gene associated with HER2 inhibitor resistance of the present invention in the probe polynucleotide. As a method of preparing the microarray by securing the probe polynucleotide on the base, a method widely known in the art may be used, and the method is not specifically limited in the present invention.

Also, hybridization of nucleic acids on the microarray and detection of the hybridization may be performed by a method widely known in the art. For the detection, for example, a nucleic acid sample is labeled with a labeling material capable of generating a detectable signal including a fluorescent material such as Cy3 and Cy5. Then, the nucleic acid sample is hybridized on the microarray. Consequently, a hybridization result can be detected by detecting a signal generated from the labeling material.

Further, the present invention provides a method for diagnosing an HER2 inhibitor-resistant cancer including: measuring, from a sample of a patient, an expression level of mRNA or protein of a gene which is associated with HER2 inhibitor resistance and satisfies at least one of conditions (1) and (2) below; and comparing the measured expression level of mRNA or protein thereof with an expression level of mRNA or protein of the corresponding gene in the control sample in order to provide information about presence and absence of HER2 inhibitor resistance.

(1) when 10 µg/ml of an HER2 inhibitor is administered to an HER2 inhibitor-resistant cell line, after 24 hours, an expression amount of a gene associated with HER2 inhibitor resistance is increased by 9% or more with respect to an expression level of the gene of the HER2 inhibitor-resistant cell line to which the HER2 inhibitor is not administered.

(2) when 10 µg/ml of an HER2 inhibitor is administered to an HER2 inhibitor-resistant cell line, after 24 hours, an expression amount of a gene associated with HER2 inhibitor resistance is increased by 5% or more with respect to an expression level of the gene of the HER2 inhibitor-resistant cell line to which the HER2 inhibitor is not administered.

Firstly, it will be described about the measuring, from a sample of a patient, an expression level of mRNA or a protein of a gene which is associated with HER2 inhibitor resistance and satisfies at least one of conditions (1) and (2) below.

The "sample of patient" includes, but not limited to, samples in which a difference in expression levels of the gene associated with HER2 inhibitor resistance appears such as tissue, cells, whole blood, serum, plasma, saliva, sputum, cerebrospinal fluid, or urea, wherein the gene is a marker gene to diagnose presence and absence of HER2 inhibitor resistance.

Since description about conditions (1) and (2) above are the same as described above, hereinafter the description is omitted.

For a specific method for measuring an expression level of mRNA or protein of the gene, expression of the gene can be detected in an mRNA or protein level, and isolation of mRNA or protein from a biological sample may be performed by using a known method.

Hereinafter, it will be described together about a specific method for measuring an expression level of mRNA or protein of the gene and comparing the measured expression level of mRNA or protein thereof with an expression level of mRNA of the corresponding gene or a protein thereof in the control sample.

The method for measuring an mRNA level includes reverse transcriptase polymerase reaction, competitive reverse transcriptase polymerase reaction, real time reverse transcriptase polymerase reaction, RNase protection analysis, Northern blotting, and DNA chip, but not limited thereto. Through the detection methods, it is possible to compare an expression amount of mRNA in a patient suspected to HER2 inhibitor resistant with an expression amount of mRNA in the control sample, preferably an HER2 inhibitor-sensitive cell line, and more preferably SKBR3, and to diagnose whether the patient suspected to have HER2 inhibitor resistance actually acquires HER2 inhibitor resistance by determining presence and absence of significant increase in expression amount of mRNA from the gene associated with HER2 inhibitor resistance.

For the measuring of an mRNA expression level, reverse transcriptase polymerase reaction or DNA chip, which use a primer specific to a gene used as a marker for diagnosing HER2 inhibitor resistance, may be used.

Specifically, in the reverse transcriptase polymerase reaction, presence and absence and degree of mRNA expression of the gene, which is used as a marker for diagnosing HER2 inhibitor resistance, may be evaluated by performing electrophoresis after reaction and then evaluating thickness and pattern of a band. The DNA chip uses a DNA chip in which the gene associated with HER2 inhibitor resistance (which corresponds to the marker) or a nucleic acid (which corresponds to a fragment of the gene) is adhered to a base such as glass at high density. mRNA is isolated from a sample, and then a terminal or internal of the mRNA is labeled with a fluorescent material to prepare a cDNA probe. Then, the probe is hybridized to the DNA chip. Thereafter, it can be determined whether HER2 inhibitor resistance is acquired or not.

In sequence, the analysis method for measuring a protein level includes western blot, ELISA, radioimmunoassay, radial immunodiffusion, Ouchterlony immunodiffusion, rocket immunoelectrophoresis, immunohistochemical staining, immunoprecipitation assay, complement fixation assay, FACS and protein chip, but not limited thereto. Through the analysis methods, it is possible to compare an amount of antibody-antigen complex formation in a patient suspected to have HER2 inhibitor resistance with an amount of antibody-antigen complex formation in the control sample, preferably an HER2 inhibitor-sensitive cell line, and more preferably SKBR3, and to diagnose whether the patient suspected to have HER2 inhibitor resistance actually acquires HER2 inhibitor resistance by determining presence and absence of significant increase in expression amounts of protein from the marker gene for diagnosing HER2 inhibitor resistance. The wording "antigen-antibody complex" means a binding product of the marker protein derived from the gene associated with HER2 inhibitor resistance, and an antibody specific to the protein. An amount of antigen-antibody complex formation may be quantitatively measured through intensity of a signal of a detection label.

For the measuring of a protein expression level, ELISA method may preferably be used.

ELISA includes various ELISA methods such as direct ELISA using a labeled antibody which recognizes an antigen adhered to a solid support; indirect ELISA using a labeled antibody which recognizes a captured antibody in a complex of an antibody recognizing an antigen adhered to a solid support; direct sandwich ELISA using a labeled antibody which recognizes an antigen in a complex of the antigen and another antibody adhered to a solid support; indirect sandwich ELISA using a labeled secondary antibody which recognizes an antibody reacting to and recognizing an antigen in a complex of the antigen and another antibody adhered to a solid support. More preferably, sandwich ELISA method as follows is performed for detection: an antibody is adhered to a solid support and reacted with a sample; and a labeled antibody, which recognizes the antibody in an antigen-antibody complex, is adhered for enzymatic luminescence, or a labeled secondary antibody for an antibody which recognizes the antibody in the antigen-antibody complex for enzymatic luminescence. By evaluating a degree of formation of the complex of the antibody and the marker protein of HER2 inhibitor resistance, it can be evaluated whether HER2 inhibitor resistance is acquired or not.

Preferably, western blot may be used, wherein the western blot uses one or more antibody to the marker for diagnosing HER2 inhibitor resistance. Whole proteins are isolated from a sample, electrophoresed to separate proteins depending on the size, transferred to a nitrocellulose membrane, and reacted with an antibody. By evaluating an amount of a produced protein by expression of the gene through a method of evaluating an amount of a produced antigen-antibody complex using a labeled antibody, it can be evaluated whether HER2 inhibitor resistance is acquired or not. The detection method includes a method of investigating an expression amount of the marker gene in cells acquiring HER2 inhibitor resistance and an expression amount of the marker gene of HER2 inhibitor in the control sample, preferably an HER2 inhibitor-sensitive cell line, and more preferably SKBR3. A level of mRNA or protein may be expressed by an absolute (e.g., μg/ml) or relative (e.g., relative signal intensity) difference in the marker protein.

Preferably, immunohistochemical staining may be used, wherein the immunohistochemical staining uses one or more antibody to the marker for diagnosing HER2 inhibitor resistance. A sample is taken from a patient and fixed. Then, a paraffin-embedded block was prepared by a method widely known in the art. The block is made into slides having a thickness of several μm, and the slides are adhered to a glass slide. Then, the paraffin-embedded block may be reacted with any selected one among the antibodies above by a known method. Then, unreacted antibodies are washed. By labeling with one of the detection label described above, it can be determined whether the antibody is labeled or not on a microscope.

According to a preferred embodiment of the present invention, a protein chip may be used, wherein, in the protein chip, one or more antibody to the marker for diagnosing HER2 inhibitor resistance are arranged at a determined position on a base and secured at a high density. In the method for analyzing a sample by using the protein chip, it can be evaluated whether HER2 inhibitor resistance is acquired or not by: isolating a protein from the sample; hybridizing the isolated protein with protein chip to form an antigen-antibody complex; and reading the result to evaluate presence or expression degree of the protein.

Through the detection methods, it can be diagnosed whether a patient suspected to have HER2 inhibitor resistance actually has HER2 inhibitor resistance by comparing an expression level of an HER2 inhibitor-resistant gene in the patient suspected to have HER2 inhibitor resistance with an expression level of the corresponding gene in the control sample, preferably an HER2 inhibitor-sensitive cell line, and more preferably SKBR3. Namely, an expression level of the marker according to the present invention is measured from cells of the patient suspected to have HER2 inhibitor resistance. An expression level of the maker according to the present invention is measured in the control sample, preferably an HER2 inhibitor-sensitive cell line, and more preferably SKBR3. Both measured expression levels are compared. When the marker according to the present invention is overexpressed when compared with the expression level in the control sample, preferably an HER2 inhibitor-sensitive cell line, and more preferably SKBR3 cell line, cells assumed HER2 inhibitor resistant may be predicted as HER2 inhibitor-resistant cells.

Also, the present invention includes a method for diagnosing an HER2 inhibitor-resistant cancer by comparing an expression level of a gene associated with HER2 inhibitor resistance in an HER2-positive cancer patient with an expression level of the corresponding gene in the control sample to provide information required to predict prognosis of the HER2-positive cancer patient about HER2 inhibitor administration.

The HER2 inhibitor, gene associated with HER2 inhibitor resistance, and method of measuring an expression level of the gene are same as described above. The control sample may preferably be an HER2 inhibitor-sensitive cell line, and more preferably SKBR3 cell line.

The present invention will be described in more detail with reference to the following examples, however it will be appreciated that the following examples are intended to help understanding of the present invention, not to limit the scope of the present invention.

<Example 1>—Selection of HER2 Inhibitor-Resistant Network and Gene Associated with HER2 Inhibitor Resistance To specifically describe a herceptin-resistant network, the association rule [Pathway-based evaluation et al., (2012) PLoS One, 7:e31685] capable of identifying all possible subset of signaling pathways (based on expression and KEGG pathway in FIG. 1) was applied. The rule was applied to the preclinical dataset [GEO: GSE15043] (BT474 drug-sensitive (parent cell) and four BT474 daughter subclones are selected for resistance to 1.0 and 0.2 μM herceptin by persistent growth). The subset (or sub-pathway) includes an edge (for example, activation, and inhibition) in addition to a node. The sub-pathways associated with drug resistance may be expressed by the network in FIG. 2 by using cytoscape software forming 4502 sub-pathways having 916 gene entries.

Then, through various preclinical datasets about herceptin-resistant ([GEO: GSE15376] [Molecular profiling et al., (2009) PLoS One, 4:e6146], [ArrayExpress: E-TABM-157] [A collection of breast cancer cell lines et al., (2006) Cancer Cell, 10:515-527) and related clinical datasets, reproducible gene entries included in the network were found. Since HER2-positive cells (i.e., SKBR3, and BT474) were herceptin-responsive and HER2-negative cells (i.e., MCF7, and MDA-MB-231) were herceptin-unresponsive, HER2-positive cells and HER2-negative cells in the two preclinical datasets were compared. Moreover, the clinical dataset was checked with an HER2-positive recurrence breast cancer derived from The Cancer Genome Atlas⌐ and ⌐Netherlands Cancer Institute⌐. Consequently, as shown in FIG. 3, 32 upregulated genes can be selected, wherein the genes are common in datasets of four authorities for upregulated genes associated with resistance to herceptin which is an HER2 inhibitor.

<Example 2>—Preclinical Evaluation of Expression Level of Selected HER2 Inhibitor Resistance-Associated Gene after HER2 Inhibitor Treatment For genes in Table 1 below among the selected HER2 inhibitor resistance-associated gene, expression levels after an HER2 inhibitor treatment were evaluated in the HER2 inhibitor-sensitive cell line, i.e., SKBR3 and HER2 inhibitor-resistant cell line, i.e., JIMT-1. The used human SKBR3 and JIMT-1 cells were provided from a public institution, American Type Culture Collection (ATCC). The SKBR3 and JIMT-1 human breast cancer cell lines were used within 6 months after resuscitation. SKBR3 cells were cultured in McCoy's 5A medium (Sigma-aldrich, USA), and JIMT-1 cells were cultured in DMEM medium (Hyclone, Thermo Fisher, USA) under the culture condition of 37° C., 5% carbon dioxide, and 10% of introduced FBS (Hyclone). Then, $2.5 \times 10^5$ number of cells were seeded and cultured under 70-80% of normoxic atmosphere. Thereafter, each of two cell lines was respectively cultured under 10 μg/ml herceptin treated state and herceptin-untreated state for 4 days.

To evaluate expression levels of genes associated with HER2 inhibitor resistance over time, gene expression levels of herceptin-treated SKBR3 and JIMT-1/herceptin-untreated SKBR3 and JIMT-1 were measured at 24 hours and 48 hours after herceptin treatment by the method as follows.

To isolate total RNA, RNA was isolated from cell lysates by using Isol-RNA lysis reagent (5PRIME Co., Germany). Then, to obtain a template for RT-PCR analysis, RNA was synthesized into cDNA by ReverTra Ace® qPCR RT Master Mix (Toyobo, Japan) containing gDNA remover kit. Qualitative PCR was performed by using CFX384 Touch™ Real-Time PCR Detection System (Biorad Co.) according to the manufacturer's protocol by using iQ™ SYBR® Green Supermix reagent (Biorad Co.). All processes were performed in accordance with manufacturer's protocol. The sequence of used primer is as Table 1 below. The results analyzed through the process were shown in FIGS. 4 and 5.

TABLE 1

| Forward Primer | Forward Primer Sequence | Seq. No. | Reverse Primer | Reverse Primer Sequence | Seq. No. | Source |
|---|---|---|---|---|---|---|
| ACTB-F | TGGACATCCGC AAAGACCTG | (Seq. No. 1) | ACTB-R | TCTTCATTGTGC TGGGTGCC | (Seq. No. 2) | Manuel |
| ARHGEF12-F | CGGCTACAGTT ATTGCAGGA | (Seq. No. 3) | ARHGEF12-R | TCTTGGCCTCTT GGATCTCT | (Seq. No. 4) | Genescript |
| ATF4-F | AGTGGCATCTG TATGAGCCCA | (Seq. No. 5) | ATF4-R | GCTCCTATTTGG AGAGCCCCT | (Seq. No. 6) | RTPrimerDB |
| CHEK2-F | CCCAAGGCTCC TCCTCACA | (Seq. No. 7) | CHEK2-R | AGTGAGAGGACT GGCTGGAGTT | (Seq. No. 8) | RTPrimerDB |
| CTNNA1-F | GCCAGTTTCTC AAGGAGGAG | (Seq. No. 9) | CTNNA1-R | AGGGATCATCTG CGAACTCT | (Seq. No. 10) | Genescript |
| CYCS-F | TGGCTAGTTGT GGCGTTTAG | (Seq. No. 11) | CYCS-R | TGAGCCTGGGAA ATAGAGGT | (Seq. No. 12) | Genescript |
| EGF-F | CTGACACTGAG GATGGGATG | (Seq. No. 13) | EGF-R | CCCATTCTTGAG GTCTTGGT | (Seq. No. 14) | Genescript |
| EGLN2-F | AGGCTCTCCCT CAGTTACCA | (Seq. No. 15) | EGLN2-R | AACTCTCCACTC CCATCCTG | (Seq. No. 16) | Genescript |
| ENAH-F | TGTGCTGGGAG ACTCTTCTG | (Seq. No. 17) | ENAH-R | CAAGTGGTCCCA AGACAATG | (Seq. No. 18) | Genescript |
| EPAS1-F | TGCTCCCACGG CCTGTAC | (Seq. No. 19) | EPAS1-R | TTGTCACACCTA TGGCATATCACA | (Seq. No. 20) | RTPrimerDB |
| FARP2-F | ACCTGGTGGGC ATAGAGAAC | (Seq. No. 21) | FARP2-R | CCTTCTTGGTGA GCTTGTGA | (Seq. No. 22) | Genescript |
| ICOSLG-F | CTGCAGAATGA CACCGTCTT | (Seq. No. 23) | ICOSLG-R | CTCTATGCAGCA GCCAATGT | (Seq. No. 24) | Genescript |
| JUP-F | TCAGCAGCAAG GGCATCAT | (Seq. No. 25) | JUP-R | TGGGTGTAAGTG GTGGTTTTCTT | (Seq. No. 26) | RTPrimerDB |
| LIMK-F | ACTGGAGCCTG AGAGCAGAG | (Seq. No. 27) | LIMK-R | CTTGATGGTGAC CTTCCCTT | (Seq. No. 28) | Genescript |
| MAPKAPK5-F | CAAGCCAGCCA AGTAACAAA | (Seq. No. 29) | MAPKAPK5-R | TCAGGCTTGAGG TCTCTGTG | (Seq. No. 30) | Genescript |
| PER2-F | GTGCAGTGGAG CAGATTCTT | (Seq. No. 31) | PER2-R | TGGTAGCGGATT TCATTCTC | (Seq. No. 32) | Genescript |
| PTPRF-F | TCGGAGCCTGT AACCTACTATG | (Seq. No. 33) | PTPRF-R | CACACCATCCAC CTCCTGAA | (Seq. No. 34) | RTPrimerDB |
| RAD51-F | AGAATTCCGAA CTGGGAAGA | (Seq. No. 35) | RAD51-R | GCCTTTCCTTCA CCTCCAC | (Seq. No. 36) | Genescript |

TABLE 1-continued

| Forward Primer | Forward Primer Sequence | Seq. No. | Reverse Primer | Reverse Primer Sequence | Seq. No. | Source |
|---|---|---|---|---|---|---|
| RPS6KA5-F | ATCAGAACGGCTACGATGAG | (Seq. No. 37) | RPS6KA5-R | GAGATTGGAAGGGAACCTGT | (Seq. No. 38) | Genescript |
| SMAD1-F | TACGCCCCCACCTGCTTAC | (Seq. No. 39) | SMAD1-R | TTTGTGTCCATCGGCTGAGA | (Seq. No. 40) | RTPrimerDB |
| STAT3-F | GATCCAGTCCGTGGAACCAT | (Seq. No. 41) | STAT3-R | ATAGCCCATGATGATTTCAGCAA | (Seq. No. 42) | RTPrimerDB |
| TIAM1-F | CTGGGATAGACCACAACAGC | (Seq. No. 43) | TIAM1-R | TGAGGCAGAAGACAAAGTCC | (Seq. No. 44) | Genescript |
| TICAM1-F | ATTGACGGTGTTTCGGACT | (Seq. No. 45) | TICAM1-R | GGACTGGCTGATTTCCAAGT | (Seq. No. 46) | Genescript |
| TJP2-F | CACGAGGAGAGCATAAGGAA | (Seq. No. 47) | TJP2-R | CGGGCTATTGTCCCTAAGTT | (Seq. No. 48) | Genescript |
| TPM1-F | TTCTCTGAACAGACGCATCC | (Seq. No. 49) | TPM1-R | CTCAGCTTCCTCCAGCTTCT | (Seq. No. 50) | Genescript |
| VAMP4-F | ATCGGATAATGCAACAGCTT | (Seq. No. 51) | VAMP4-R | AAAGGATAGCAGCAACCAAA | (Seq. No. 52) | Genescript |

Specifically, FIG. 4 is a graph showing expression amounts of 25 genes associated with herceptin resistance at 24 hours after 10 μg/ml herceptin administration into JIMT-1, which is a herceptin-resistant cell line, and SKBR3, which is a herceptin-sensitive cell line, according to a preferred embodiment of the present invention. It can be found that the herceptin-resistant cell line, JIMT-1, showed increased amounts of expression of most genes, whereas the herceptin-sensitive cell line, SKBR3, showed reduced amounts of expression of most genes.

Specifically, FIG. 5 is a graph showing expression amounts of 25 genes associated with herceptin resistance at 48 hours after 10 μg/ml herceptin administration into JIMT-1, which is a herceptin-resistant cell line, and SKBR3, which is a herceptin-sensitive cell line, according to a preferred embodiment of the present invention. It can be found that the herceptin-resistant cell line, JIMT-1, showed remarkably increased amounts of expression of almost genes, whereas the herceptin-sensitive cell line, SKBR3, showed remarkably reduced amounts of expression of almost genes.

<Example 3>—Evaluation of Cell Viability after Knock-Down of Gene Associated with HER2 Inhibitor Resistance and HER2 Inhibitor Treatment Firstly, 4,000 number of SKBR3 cells and 2,000 number of JIMT-1 cells were plated on a 384-well plate (Greiner Co., Germany). Then, cells were plated triplicate, and 6 images were taken for each well. siRNA for knock-down of a gene associated with HER2 inhibitor resistance was purchased from Thermo Scientific, Co., and prepared such that final concentration became 50 nM. 0.5 μl of DharmaFECT1 was used for each well. At 48 hours after the siRNA treatment, cells were treated with 10 μg/ml of herceptin. At 48 hours after herceptin treatment, cells were fixed with 4% paraformaldehyde, and stained by using HCS Cellmask (H32712, Molecular Probes, Thermo Scientific). A nucleus was stained with Draq5 (Cell Signaling Technology Co.) to count surviving cells. The result was shown in FIG. 6. Opera high content screening system, (OPERA, PerkinElmer Co.) was used for the imaging and cell counting. In addition, for siRNA data analysis, PRISM (version 5) software was used.

Specifically, FIG. 6 is a graph showing the cell viability test of an HER2 inhibitor-resistant cell line (JIMT-1) and an HER2 inhibitor-sensitive cell line (SKBR3) in which a gene associated with HER2 inhibitor resistance was knocked down. Any one of gene among the selected HER2 inhibitor resistance-associated gene was knocked down, and an HER2 inhibitor was treated. Then, cell viability was evaluated. Consequently, it can be found that cell viability of the HER2 inhibitor-resistant cell line, JIMT-1, was reduced by herceptin which is an HER2 inhibitor. From the result, it is considered that the cell having knock-down of any one of gene among selected 32 genes, which are associated with HER2 inhibitor resistance, recovers sensitivity to the HER2 inhibitor, although the cell (for example, JIMT-1) was resistant to the HER2 inhibitor.

Figure 10:
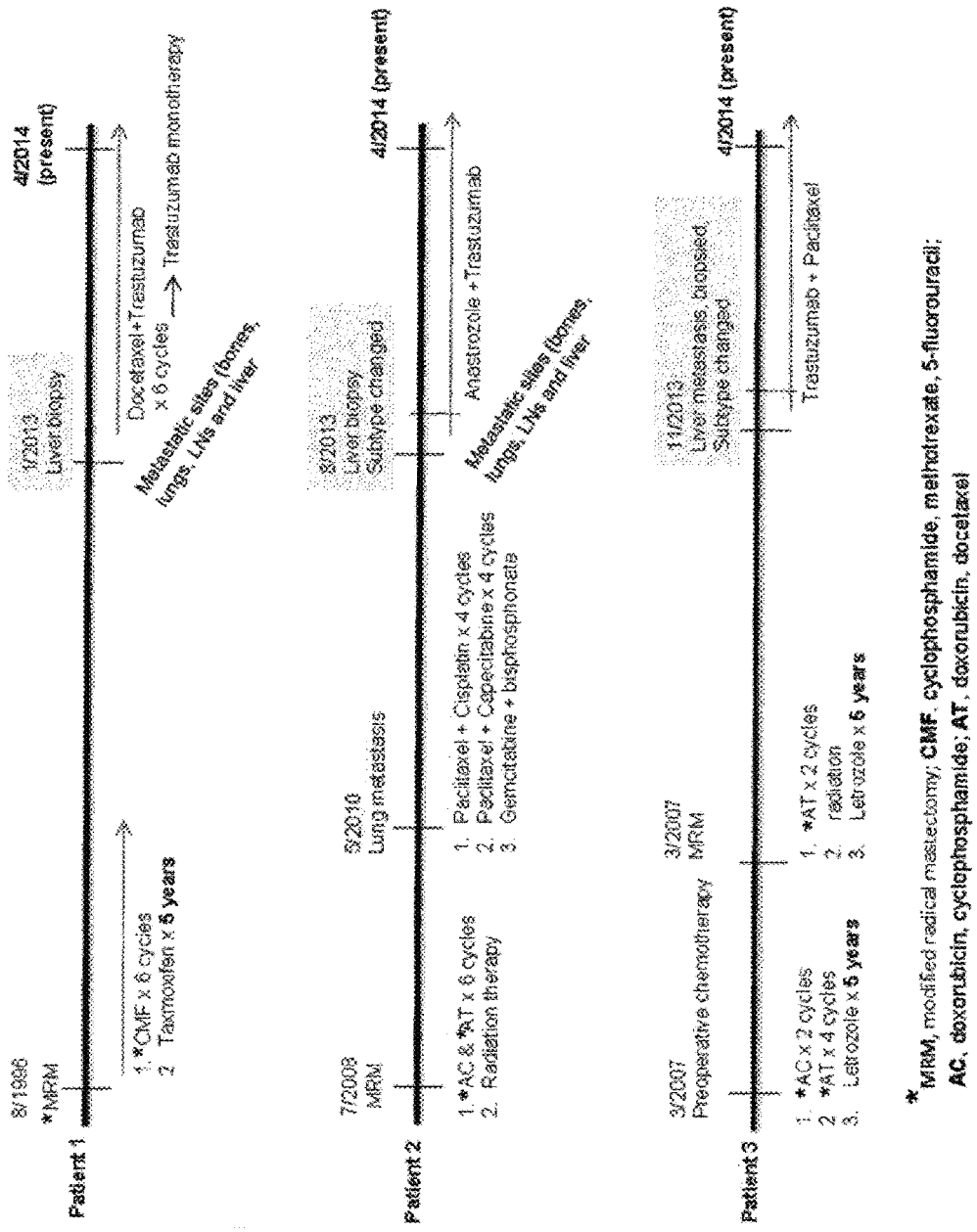
FIG. 10 is a schematic diagram showing clinical information about an HER2 inhibitor-sensitive patient used in the clinical test according to a preferred embodiment of the present invention.

<Example 4>—Evaluation of Expression Level of Selected HER2 Inhibitor Resistance-Associated Gene after HER2 Inhibitor Treatment Total 6 breast cancer samples were used as a specimen for clinical test of an expression level of the selected HER2 inhibitor resistance-associated gene after an HER2 inhibitor treatment. A subject patient, from whom the breast cancer sample was taken, agreed with a use of tissue of clinical specimen for research purpose according to the present invention, and also approval from Institutional Review Board (IRB) of National Cancer Center in Korea was received. Histological classification and tumor stages of subject patients, from whom the 6 breast cancer samples were taken, were reviewed by a pathologist of National Cancer Center. Reviewed clinical information for each patient is shown in FIGS. 10 and 11.

Figure 11:
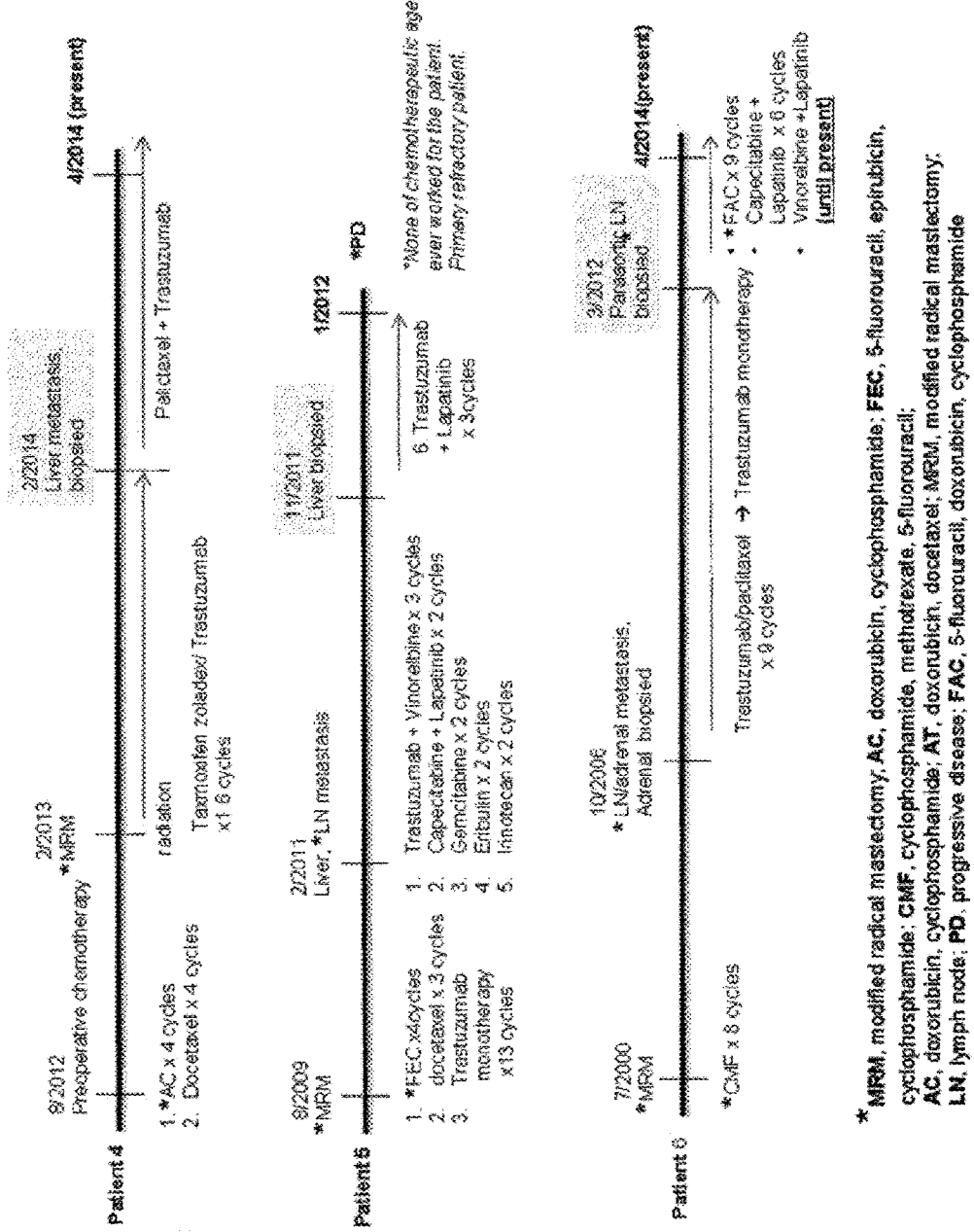
FIG. 11 is a schematic diagram showing clinical information about an HER2 inhibitor-resistant patient used in the clinical test according to a preferred embodiment of the present invention.

Three samples among total 6 breast cancer samples are herceptin-sensitive samples (patients 1 to 3, FIG. 10), and the rest three samples are herceptin-resistant samples (patients 4 to 6, FIG. 11). Expression levels of selected HER2 inhibitor resistance-associated genes for each of 6 breast cancer samples were measured by the method as follows.

To isolate total RNA, RNA was isolated from cell lysates by using Isol-RNA lysis reagent (5PRIME Co., Germany). Then, to obtain a template for RT-PCR analysis, RNA was synthesized into cDNA by ReverTra Ace qPCR RT Master Mix (Toyobo, Japan) containing gDNA remover kit. Qualitative PCR was performed by using CFX384 Touch™ Real-Time PCR Detection System (Biorad Co.) according to the manufacturer's protocol by using iQ™ SYBR® Green Supermix reagent (Biorad Co.). All processes were performed in accordance with manufacturer's protocol. The sequence of used primer is as Table 1 above. Results analyzed through the process were shown in FIGS. 7 to 9. An expression level for a particular gene in each sample shown in FIGS. 7 to 9 was expressed by a relative value based on an amount of expression of ACTB gene in each sample.

Specifically, FIGS. 7 to 9 are graphs showing clinical test results for 25 genes among 32 genes associated with HER2 inhibitor resistance. An expression degree of each of 32 genes was evaluated in 3 patients sensitive to the HER2 inhibitor and 3 patients resistant to the HER2 inhibitor. Consequently, it can be found that ATF4, CHEK2, EGF, EGLN2, ENAH, FARP2, ICOSLG, JUP and RAD5 genes were remarkably downregulated in cancer cells taken from 3 patient group (patients 1 to 3) sensitive to herceptin, which is an HER2 inhibitor, whereas those genes were remarkably upregulated, in contrast, in cancer cells taken from 3 patient group (patients 4 to 6) resistant to herceptin, which is an HER2 inhibitor.

<Example 5>—Evaluation of Cell Viability of HER2 Inhibitor-Sensitive Cell Line and HER2 Inhibitor-Resistant Cell Line with Lapse of Days Depending on HER2 Inhibitor Treatment and Evaluation of Amount of Expression of HER2 with Lapse of Days To evaluate expression of HER2 protein and sensitivity to herceptin drug, which is an HER2 inhibitor, of SKBR3 and JIMT-1 (which respectively correspond to an HER2 inhibitor-sensitive cell line and HER2 inhibitor-resistant cell line), cell viability and expression degrees of HER2 protein in SKBR3 and JIMT-1 cells upon herceptin treatment were measured.

Specifically, the used human SKBR3 and JIMT-1 cells were provided from a public institution, American Type Culture Collection (ATCC). The SKBR3 and JIMT-1 human breast cancer cell lines were used within 6 months after resuscitation. SKBR3 cells were cultured in McCoy's 5A medium (Sigma-aldrich, USA), and JIMT-1 cells were cultured in DMEM medium (Hyclone, Thermo Fisher, USA) under the culture condition of 37° C., 5% carbon dioxide, and 10% of introduced FBS (Hyclone). Then, $2.5 \times 10^5$ number of cells were seeded and cultured under 70-80% of normoxic atmosphere. Thereafter, each of two cell line was respectively cultured under 10 μg/ml herceptin-treated and herceptin-untreated states for 4 days.

During the culturing process, cell viability was evaluated at each day. A method of evaluating cell viability was as follows: after treatment, cells were fixed at each day with 4% paraformaldehyde, and stained by using HCS Cellmask (H32712, Molecular Probes, Thermo Scientific); nucleuses were stained with Draq5 (Cell Signaling Technology Co.); and then, surviving cells were counted. The cell counting was performed by using opera high content screening system (OPERA, PerkinElmer Co.), and the result were shown in FIG. 12.

Also, during the culturing process, an amount of HER2 expression was evaluated at each day. Specifically, after herceptin treatment, cells at each day were washed with phosphate buffer saline twice, and western blot was performed in accordance with the specific method in the prior art document [Antitumor agent et al., (2011) *Cancer Chemother Pharmacol*, 68:405-413]. An expression degree was measured by using imaging experiment software, Image Lab software (Bio-Rad Co.), and the result was shown in FIG. 13 below. β-actin was used to check whether the procedure and analysis were appropriately performed by the specific method as in the prior art document [Antitumor agent PX-12 et al., (2011) *Cancer Chemother Pharmacol*, 68:405-413] by using 2(-delta-delta C(T)) method as in the prior art document [Analyzing real-time PCR data et al., (2008) *Nature Protocols*, 3:1101-1108].

Figure 12:
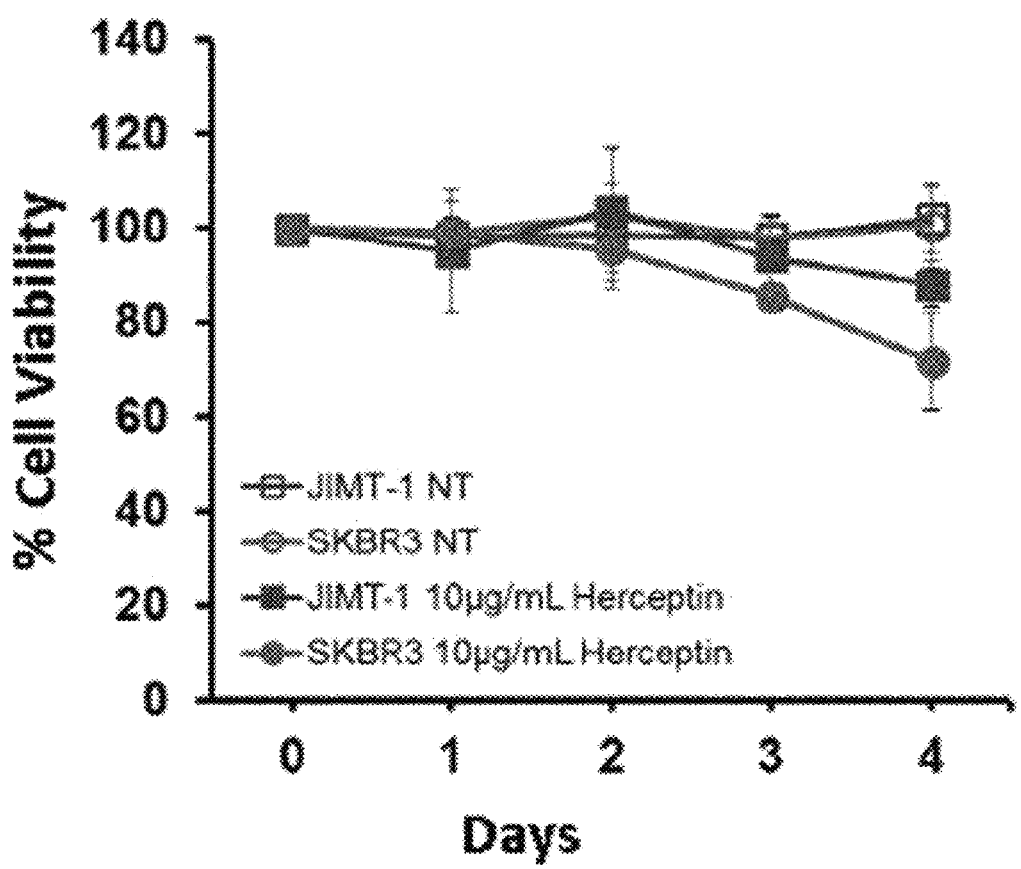
FIG. 12 is a graph showing survival curves of the HER2 inhibitor-sensitive cell line and HER2 inhibitor resistant cell line depending on HER2 inhibitor treatment with the lapse of days according to a preferred embodiment of the present invention.

Specifically, in FIG. 12, it can be found that, after 10 μg/ml herceptin treatment and 4 days of culture, cell viability of JIMT-1 cells was only reduced by 15%. In the contrary, it can be found that, after 4 days from herceptin treatment, cell viability of SKBR3 cells was reduced by more than 30% when compared with herceptin-untreated SKBR3 cells. From the result, it can be found that JIMT-1 cells are resistant to herceptin, however SKBR3 cells are sensitive to herceptin.

Specifically, in FIG. 13, it can be found that HER2 protein in JIMT-1 cells was downregulated by more than 90% at 4 days after herceptin treatment. Meanwhile, it can be found that, even in herceptin-untreated JIMT-1 cells, HER2 protein was downregulated by about 60% during the same period of time. In the contrary, it can be found that SKBR3 cells showed almost no change in HER2 expression.

From the result, it can be found that HER2 internalization or shedding of extracellular domain of HER2 is a mechanism of herceptin resistance.

What is claimed is:

1. A method for providing information about prognosis of an HER2-positive breast cancer patient about administration of trastuzumab and treating the HER2-positive breast cancer patient, the method comprising:
    (a) obtaining a sample from the HER2-positive breast cancer patient who are taking the trastuzumab:
    (b) treating the sample with the trastuzumab for 24 to 48 hours;
    (c) measuring an expression level of mRNA of ENAH gene and an expression level of HER2 protein from the sample of (b);
    (d) diagnosing the HER2-positive breast cancer patient having trastuzumab resistance when the measured expression level of mRNA of ENAH gene is higher than an expression level of mRNA of the corresponding gene in the sample before treating with the trastuzumab, and the measured expression level of HER2 protein is lower than an expression level of the corresponding protein in the sample before treating with the trastuzumab; and
    (e) administering a second-line drug to the patient diagnosed as having trastuzumab resistance.

2. A method for diagnosing a presence or an absence of trastuzumab resistance in an HER2-positive breast cancer patient and treating the HER2-positive breast cancer patient, the method comprising:
    (a) obtaining a sample from the HER2-positive breast cancer patient;

(b) treating the sample with the trastuzumab for 24 to 48 hours;
(c) measuring an expression level of mRNA of ENAH gene and an expression level of HER2 protein from the sample of (b);
(d) diagnosing the HER2-positive breast cancer patient having trastuzumab resistance when the measured expression level of mRNA of ENAH gene is higher than an expression level of mRNA of the corresponding gene in the sample before treating with the trastuzumab, and the measured expression level of HER2 protein is lower than an expression level of the corresponding protein in the sample before treating with the trastuzumab; and
(e) administering a second-line drug to the patient diagnosed as having trastuzumab resistance.

* * * * *